(12) United States Patent
Blike

(10) Patent No.: US 6,743,172 B1
(45) Date of Patent: Jun. 1, 2004

(54) SYSTEM AND METHOD FOR DISPLAYING MEDICAL PROCESS DIAGRAMS

(75) Inventor: George T. Blike, Norwich, VT (US)

(73) Assignees: Alliance Pharmaceutical Corp., San Diego, CA (US); The Trustees of Dartmouth College, Hanover, NH (US)

(*) Notice: Subject to any disclaimer, the term of this patent is extended or adjusted under 35 U.S.C. 154(b) by 41 days.

(21) Appl. No.: 09/706,512

(22) Filed: Nov. 3, 2000

Related U.S. Application Data

(62) Division of application No. 09/020,472, filed on Feb. 9, 1998, now Pat. No. 6,234,963.
(60) Provisional application No. 60/071,510, filed on Jan. 14, 1998.

(51) Int. Cl.[7] .................................................. A61F 5/00
(52) U.S. Cl. ....................... 600/300; 600/485; 600/500; 600/504; 600/526
(58) Field of Search ................................. 600/300–301, 600/485, 500–504, 505, 526

(56) References Cited

U.S. PATENT DOCUMENTS

| | | | |
|---|---|---|---|
| 3,811,040 A | 5/1974 | Weinfurt et al. | |
| 4,562,843 A | 1/1986 | Djordjevich et al. | 128/672 |
| 5,101,825 A | 4/1992 | Gravenstein et al. | 128/633 |
| 5,103,828 A * | 4/1992 | Sramek | 600/485 |
| 5,183,051 A | 2/1993 | Kraidin et al. | 128/687 |
| 5,217,019 A | 6/1993 | Hughes | 128/668 |
| 5,262,944 A | 11/1993 | Weisner et al. | 600/300 |
| 5,316,005 A | 5/1994 | Tomita | 600/500 |
| 5,398,680 A | 3/1995 | Polson et al. | 126/633 |
| 5,546,943 A | 8/1996 | Gould | |
| 5,921,920 A * | 7/1999 | Marshall et al. | 600/300 |
| 6,390,977 B1 * | 5/2002 | Faithfull et al. | 600/300 |

FOREIGN PATENT DOCUMENTS

| | | |
|---|---|---|
| EP | 0059868 | 9/1982 |
| EP | 0 505 037 A1 | 2/1992 |
| EP | 0 901 798 A1 | 6/1998 |
| WO | 90/04353 | 5/1990 |
| WO | 90/07357 | 7/1990 |
| WO | 92/11804 | 7/1992 |
| WO | 94/23643 | 10/1994 |
| WO | 97/20592 | 6/1997 |

OTHER PUBLICATIONS

Cole et al, "Metaphor Graphics to Support Integrated Decision making with Respiratory Data, "INternational Journal of Clinical Monitoring and Computing, 1993, pp. 91–100.*
Fan, et al. "Effects of Hematocrit Variations on Regional Hemodynamics and Oxygen Transport in the Dog" Am.J.Physiol.238:H545–H552 (1980).
Lundsgaard–Hansen. P. "Hemodilution–New Clothes for an Anemic Emperor" Vox Sang 36:321–336 (1979).
Lundsgaard–Hansen. et al. "Is There a Generally Valid, Minimum Acceptable Hemogloblin Level?" Infusiontherapie 16:167–175 (1989).
Robertie, et al. "Safe Limits of Isovolemic Hemodilution and Recommendations For Erythrocyte Transfusion" Int'l Anesthesiology Clinics 28(4): 197–204 (1990).

(List continued on next page.)

*Primary Examiner*—Robert L. Nasser
(74) *Attorney, Agent, or Firm*—Sheppard, Mullin, Richter & Hampton LLP

(57) ABSTRACT

A system and method is described for determining and graphically displaying oxygenation states of a patient in real time. The system is non-invasive and can display information to a physician that is intuitive. Various display objects are described for illustrating the output of oxygenation values. The display objects reflect the in vivo physiology that they measure, thus making interpretation of the measured values very intuitive.

12 Claims, 18 Drawing Sheets

OTHER PUBLICATIONS

Severinghaus, John "Blood Gas Calculator" J.Appl.Physiol. 21(3): 1108–1116 (1966).

Hint, H. The Pharmacology of Dextran and the Physiological Background for the Clinical Use of Rheomacrodex and Macrodex: Acta Anasthesiologica Belgica 2:119–138 (1968).

Kelman, G. Richard "Digital Computer Subroutine for the Conversion of Oxygent Tension into Saturation" J.Appl. Physiol. 21(4):1375–1376 (1966).

Mohsenifar, et al. "Relationship Between $O_2$ Delivery and $O_2$ Consumption in the Adult Respiratory Distress Syndrome" Chest 84(3):267–271 (1983).

Shibutani, et al. "Critical Level of Oxygen Delivery in Anesthetized Man" Critical Care Med. 11(8): 640–643 (1983).

Faithfull, et al. "A Program to Calculate Mixed Venous Oxygen Tension–A Guide to Transfusion?" *Oxygen Transport Tissue XVI*, Eds. Hogan, et al. pp. 41–49 (1994).

Product Brochure from Waters Instruments, Inc., Rochester, MN 55903–6117 to MRM™ 6000 Metabolic Analyzer in 7 pages.

* cited by examiner

SYSTEM AND METHOD FOR DISPLAYING MEDICAL PROCESS DIAGRAMS

RELATED APPLICATIONS

This application is a division of prior copending application Ser. No. 09/020,472, filed Feb. 9, 1998, now U.S. Pat. No. 6,234,963. This application is also related to U.S. provisional application No. 60/071,510, filed Jan. 14, 1998.

BACKGROUND OF THE INVENTION

1. Field of the Invention

This invention relates to display systems. More specifically, this invention relates to systems for displaying graphical information to physicians.

2. Description of the Related Technology

Medical display systems provide information to doctors in a clinical setting. Typical display systems provide data in the form of numbers and one-dimensional signal waveforms that must be assessed, in real time, by the attending physician. Alarms are sometimes included with such systems to warn the physician of an unsafe condition, e.g., a number exceeds a recommended value. In the field of anesthesiology, for example, the anesthesiologist must monitor the patient's condition and at the same time (i) recognize problems, (ii) identify the cause of the problems, and (iii) take corrective action during the administration of the anesthesia. An error in judgment can be fatal.

Approximately 50 percent of the more than 2000 anesthesia-related deaths per year have been found to be due to improper choices during surgery. In general, human error in anesthesia represents failure by the anesthesiologist to recognize a problem (abnormal physiology), identify the cause of the problem and take appropriate corrective action when administering an anesthetic to a patient. Anesthesia performance models, models showing the relationship between errors, incidents and accidents, and models depicting accident evolution in the anesthesia all illustrate the fact that anesthesia is a complex environment prone to errors.

Physiologic data displays of the patient's condition play a central role in allowing anesthesiologists to observe problem states in their patients and deduce the most likely causes of the problem state during surgery. As one might predict, 63 percent of the reported incidents in the Australian Incident Monitoring Study (AIMS) database were considered detectable with standard data monitors. Others have attempted to address these problems, but with only limited success.

For example, Cole, et. al. has developed a set of objects to display the respiratory physiology of intensive care unit (ICU) patients on ventilators. This set of displays integrates information from the patient, the ventilator, rate of breathing, volume of breathing, and percent oxygen inspired. Using information from object displays, ICU physicians made faster and more accurate interpretations of data than when they used alphanumeric displays. Cole published one study that compared how physicians performed data interpretation using tabular data vs. printed graphical data. However, Cole's work did not involve a system for receiving analog data channels and driving a real-time graphical display on a medical monitor.

In addition, Ohmeda, a company that makes anesthesia machines, manufacturers the Modulus CD machine which has an option for displaying data in a graphical way. The display has been referred to as a glyph. Physiologic data is mapped onto the shape of a hexagon. Six data channels generate the six sides of the hexagon. Although this display is graphical, the alphanumeric information of the display predominates. There is no obvious rational for why the physiologic data is assigned a side of the hexagon. Moreover, symmetric changes to the different signs of this geometric shape are very hard for individuals to differentiate.

In the surgical and postoperative settings, decisions regarding the need for blood transfusion normally are guided by hemoglobin (Hb) or hematocrit levels (Hct). Hematocrit is typically defined as the percentage by volume of packed red blood cells following centrifugation of a blood sample. If the hemoglobin level per deciliter of blood in the patient is high, the physician can infer that the patient has sufficient capacity to carry oxygen to the tissue. During an operation this value is often used as a trigger; i.e. if the value falls below a certain point, additional blood is given to the patient. While these parameters provide an indication of the arterial oxygen content of the blood, they provide no information on the total amount of oxygen transported (or "offered") to the tissues, or on the oxygen content of blood coming from the tissues.

For example, it has been shown that low postoperative hematocrit may be associated with postoperative ischemia in patients with generalized atherosclerosis. Though a number of researchers have attempted to define a critical Hct level, most authorities would agree that an empirical automatic transfusion trigger, whether based on Hb or Hct, should be avoided and that red cell transfusions should be tailored to the individual patient. The transfusion trigger, therefore, should be activated by the patient's own response to anemia rather than any predetermined value.

This is, in part, due to the fact that a number of parameters are important in determining how well the patient's tissues are actually oxygenated. In this regard, the patient's cardiac output is also an important factor in correlating hemoglobin levels with tissue oxygenation states. Cardiac output or CO is defined as the volume of blood ejected by the left ventricle of the heart into the aorta per unit of time (ml/min) and can be measured with thermodilution techniques. For example, if a patient has internal bleeding, the concentration of hemoglobin in the blood might be normal, but the total volume of blood will be low. Accordingly, simply measuring the amount of hemoglobin in the blood without measuring other parameters such as cardiac output is not always sufficient for estimating the actual oxygenation state of the patient.

More specifically the oxygenation status of the tissues is reflected by the oxygen supply/demand relationship of those tissues i.e., the relationship of total oxygen transport ($DO_2$) to total oxygen consumption ($VO_2$). Hemoglobin is oxygenated to oxyhemoglobin in the pulmonary capillaries and then carried by the cardiac output to the tissues, where the oxygen is consumed. As oxyhemoglobin releases oxygen to the tissues, the partial pressure of oxygen ($PO_2$) decreases until sufficient oxygen has been released to meet the oxygen consumption ($VO_2$). Although there have been advances in methods of determining the oxygenation status of certain organ beds (e.g., gut tonometry; near infrared spectroscopy) these methods are difficult to apply in the clinical setting. Therefore, the use of parameters that reflect the oxygenation status of the blood coming from the tissues i.e., the partial pressure of oxygen in the mixed venous blood ($PvO_2$; also known as the mixed venous blood oxygen tension) or mixed venous blood oxyhemoglobin saturation ($SvO_2$) has become a generally accepted practice for evaluating the global oxygenation status of the tissues.

Unfortunately, relatively invasive techniques are necessary to provide more accurate tissue oxygenation levels. In this respect, direct measurement of the oxygenation state of a patient's mixed venous blood during surgery may be made using pulmonary artery catheterization. To fully assess whole body oxygen transport and delivery, one catheter (a flow directed pulmonary artery [PA] catheter) is placed in the patient's pulmonary artery and another in a peripheral artery. Blood samples are then drawn from each catheter to determine the pulmonary artery and arterial blood oxygen levels. As previously discussed, cardiac output may also be determined using the PA catheter. The physician then infers how well the patient's tissue is oxygenated directly from the measured oxygen content of the blood samples.

While these procedures have proven to be relatively accurate, they are also extremely invasive. For example, use of devices such as the Swan-Ganz® thermodilution catheter (Baxter International, Santa Ana, Calif.) can lead to an increased risk of infection, pulmonary artery bleeding, pneumothorax and other complications. Further, because of the risk and cost associated with PA catheters, their use in surgical patients is restricted to high-risk or high-blood-loss procedures (e.g., cardiac surgery, liver transplant, radical surgery for malignancies) and high-risk patients (e.g., patients who are elderly, diabetic, or have atherosclerotic disease).

Among other variables, determination of the oxygenation status of the tissues should include assessment of the amount of blood being pumped toward the tissues (CO) and the oxygen content of that (arterial) blood ($CaO_2$). The product of these variables may then be used to provide a measure of total oxygen transport ($DO_2$). Currently, assessment of $DO_2$ requires the use of the invasive monitoring equipment described above. Accordingly, determination of $DO_2$ is not possible in the majority of surgical cases. However, in the intensive care unit (ICU), invasive monitoring tends to be a part of the routine management of patients; thus, $DO_2$ determinations are obtained more readily in this population.

Partial pressure of oxygen in the mixed venous blood or mixed venous blood oxygen tension ($PvO_2$) is another important parameter that may be determined using a PA catheter. Because of the equilibrium that exists between the partial pressure of oxygen ($PO_2$) in the venous blood and tissue, a physician can infer the tissue oxygenation state of the patient. More specifically, as arterial blood passes through the tissues, a partial pressure gradient exists between the $PO_2$ of the blood in the arteriole passing through the tissue and the tissue itself. Due to this oxygen pressure gradient, oxygen is released from hemoglobin in the red blood cells and also from solution in the plasma; the released $O_2$ then diffuses into the tissue. The $PO_2$ of the blood issuing from the venous end of the capillary cylinder ($PvO_2$) will generally be a close reflection of the $PO_2$ at the distal (venous) end of the tissue through which the capillary passes.

Closely related to the mixed venous blood oxygen tension ($PvO_2$) is the mixed venous blood oxyhemoglobin saturation ($SvO_2$) which is expressed as the percentage of the available hemoglobin bound to oxygen. Typically, oxyhemoglobin disassociation curves are plotted using $SO_2$ values vs. $PO_2$ values. As the partial pressure of oxygen ($PO_2$) decreases in the blood (i.e. as it goes through a capillary) there is a corresponding decrease in the oxygen saturation of hemoglobin ($SO_2$). While arterial values of $PO_2$ and $SO_2$ are in the neighborhood of 95 mm Hg and 97% respectively, mixed venous oxygen values ($PvO_2$, $SvO_2$) are on the order of 45 mm Hg and 75% respectively. As such $SvO_2$, like $PvO_2$, is indicative of the global tissue oxygenation status. Unfortunately, like $PvO_2$, it is only measurable using relatively invasive measures.

Another rather informative parameter with respect to patient oxygenation is deliverable oxygen ($dDO_2$). dDO2 is the amount of the oxygen transported to the tissues ($DO_2$) that is able to be delivered to the tissues (i.e. consumed by the tissues) before the $PvO_2$ (and by implication the global tissue oxygen tension) falls below a certain value. For instance the $dDO_2(40)$ is the amount of oxygen that can be delivered to the tissues (consumed by the tissues) before $PvO_2$ is 40 mm Hg while $dDO_2(35)$ is the amount consumed before the $PvO_2$ falls to 35 mm Hg.) Additional relevant parameters may be determined non-invasively. For instance, whole body oxygen consumption ($VO_2$) can be calculated from the difference between inspired and mixed expired oxygen and the minute volume of ventilation. Cardiac output may also be non-invasively inferred by measuring arterial blood pressure instead of relying on thernodilution catheters. For example, Kraiden et al. (U.S. Pat. No. 5,183,051, incorporated herein by reference) use a blood pressure monitor to continuously measure arterial blood pressure. These data are then converted into a pulse contour curve waveform. From this waveform, Kraiden et al. calculate the patient's cardiac output.

Regardless of how individual parameters are obtained, those skilled in the art will appreciate that various well established relationships allow additional parameters to be derived. For instance, the Fick equation (Fick, A. Wurzburg, *Physikalisch edizinische Gesellschaft* Sitzungsbericht 16 (1870)) relates the arterial oxygen concentration, venous oxygen concentration and cardiac output to the total oxygen consumption of a patient and can be written as:

$$(CaO_2 - CvO_2) \times CO = VO_2$$

where $CaO_2$ is the arterial oxygen content, $CvO_2$ is the venous oxygen content, CO is the cardiac output and $VO_2$ represents whole body oxygen consumption.

While the non-invasive derivation of such parameters is helpful in the clinical setting, a more determinative "transfusion trigger" would clearly be beneficial. If $PvO_2$ or $DO_2$ is accepted as a reasonable indicator of patient safety, the question of what constitutes a "safe" level of these parameters arises. Though data exists on critical oxygen delivery levels in animal models, there is little to indicate what a critical $PvO_2$ might be in the clinical situation. The available data indicate that the level is extremely variable. For instance, in patients about to undergo cardiopulmonary bypass, critical $PvO_2$ varied between about 30 mm Hg and 45 mm Hg where the latter value is well within the range of values found in normal, fit patients. Safe $DO_2$ values exhibit similar variability.

For practical purposes a $PvO_2$ value of 35 mm Hg or more may be considered to indicate that overall tissue oxygen supply is adequate, but this is implicit on the assumption of an intact and functioning vasomotor system. Similarly, the accurate determination of $DO_2$ depends on an intact circulatory system. During surgery it is necessary to maintain a wide margin of safety and probably best to pick a transfusion trigger (whether $DO_2$, $PvO_2$, $SvO_2$ or some derivation thereof) at which the patient is obviously in good condition as far as oxygen dynamics are concerned. In practice, only certain patients will be monitored with a pulmonary artery catheter. Accordingly, the above parameters will not be available for all patients leaving the majority to be monitored with the imperfect, and often dangerous, trigger of Hb concentration.

Efforts to resolve these problems in the past have not proven entirely successful. For example, Faithfull et al. (*Oxygen Transport to Tissue XVI*, Ed. M. Hogan, Plenum Press, 1994, pp. 41–49) describe a model to derive the oxygenation status of tissue under various conditions. However, the model is merely a static simulation allowing an operator to gauge what effect changing various cardiovascular or physical parameters will have on tissue oxygenation. No provisions are made for continuous data acquisition and evaluation to provide a dynamic representation of what may actually be occurring. Accordingly, the model cannot be used to provide real-time measurements of a patient's tissue oxygenation under changing clinical conditions.

Thus, what is needed in the art is a relatively non-invasive system for intuitively displaying physiological information to a physician. The system described below provides such a system to improve a physician's interpretation of patient data. Other aspects of the system will become apparent in the description that follows.

SUMMARY

Embodiments of the invention provide for the real-time determination and display of one or more values that accurately reflect the physiological condition of a patient. Preferred values include the global oxygenation and cardiovascular status of the patient. Each of these values can be displayed as intuitive medical process diagrams to assist the physician in understanding the medical condition of their patient. Moreover, many of the displayed values can be advantageously determined without invasive procedures on the patient. As such, the display system discussed herein may be used to safely and intuitively monitor the physiological condition of patients and adjust therapeutic parameters based on the displayed values.

In preferred embodiments, the present invention provides for the determination and real-time display of physiologically important oxygenation parameters indicative of a patient's tissue oxygenation status such as, for example, total oxygen transport ($DO_2$), deliverable oxygen transport ($dDO_2$), mixed venous blood oxyhemoglobin saturation ($SvO_2$) and mixed venous blood oxygen tension ($PvO_2$). The invention may also be used to provide a supply/demand ratio ($dDO_2/VO_2$), another oxygenation parameter, that allows a physician to accurately monitor and adjust the oxygen status of a patient using a single numerical value.

It will be appreciated that the derived oxygenation parameters may be used alone or, more preferably, in combination to provide an indication as to global tissue oxygenation levels. As such, the invention may be used as an uncomplicated, real-time intervention trigger in clinical settings without the risks associated with conventional invasive monitoring equipment.

More specifically, by establishing the minimum acceptable $PvO_2$, $SvO_2$, $dDO_2$ or $DO_2$ for the individual patient, the attending physician is provided with a simple trigger point where intervention is indicated. For example, based on clinical experience, a physician may determine that the $PvO_2$ of a patient should not be below 35 mm Hg or that the $DO_2$ should remain above 600 ml/min in order to provide adequate oxygenation. (Preferably, the clinician will have access to each of the oxygenation parameters and can display one or more values as desired. In a particularly preferred embodiment, the system will provide a supply/demand ratio ($dDO_2/VO_2$) for a selected $PvO_2$ thereby allowing the physician to address the needs of the patient based on a single value. In this embodiment, a value of one or greater indicates the $PvO_2$ (and hence global tissue oxygenation) is higher than the established trigger point.

Particularly preferred embodiments provide a continuous (beat-to-beat) measurement of cardiac output (CO), using inputs from an indwelling catheter placed in a peripheral artery. In this respect an apparatus such as the Modelflow™ system (TNO-Biomedical Instrumentation, Amsterdam), can optionally be used in conjunction with the present invention to provide the CO measurement continuously in real-time. Cardiac output may be computed using an algorithm that simulates the behavior of the human aorta and arterial system via a three-element, nonlinear model of aortic input impedance. Cardiac output computed using this model has been validated against cardiac output determined by thermodilution. In addition to cardiac output, the following hemodynamic information can be derived from systems like Modelflow™ on a beat-to-beat basis: systolic, diastolic, and mean arterial pressure; pulse rate; stroke volume; and peripheral vascular resistance.

Embodiments of the invention also determine the arterial oxygen content ($CaO_2$) of the patient for use in deriving the desired values. Specifically, in determining the arterial oxygen content ($CaO_2$), one or more numerical values may be used corresponding to the patient's hemoglobin concentration, arterial oxygen tension ($PaO_2$), arterial carbon dioxide tension ($PaCO_2$), arterial pH and body temperature. These numerical values may be obtained from a blood chemistry monitor or entered manually. Particularly preferred embodiments employ a blood chemistry monitor to obtain the desired values contemporaneously with the measurement of the cardiac output values. Additionally, the oxygen consumption of the patient ($VO_2$) is determined, preferably by gas analysis or metabolic rate determination.

As previously indicated, the embodiments of the invention further provide methods and apparatus that may be used to monitor the tissue oxygenation status of a patient using a supply/demand ratio. Accordingly, one embodiment of the invention is directed to a relatively non-invasive method for monitoring, in real-time, tissue oxygenation status of a patient comprising the determination of a supply/demand ratio ($dDO_2/VO_2$). Similarly, another embodiment is directed to a relatively non-invasive apparatus for determining, in real-time, tissue oxygenation status of a patient. The apparatus may include instructions for determining a supply/demand ratio ($dDO_2/VO_2$). The calculations, values and equipment necessary to provide the desired ratios are as described throughout the present specification.

In all cases it must be emphasized that, while preferred embodiments of the invention include a blood chemistry monitor and/or pressure transducers (i.e. for CO), they are not essential components of the present invention and are not necessary for practicing the disclosed methods. For example, a physician could manually measure blood gas levels, body temperatures and Hg concentrations and then enter this information into the system via the keyboard. Other methods of measuring cardiac output could be used, such as ultrasound, thoracic impedance, or partial CO2 rebreathing method.

Those skilled in the art will further appreciate that oxygenation constants are numerical values primarily related to the physical characteristics of oxygen carriers or to the physiological characteristics of the patient. Such oxygenation constants include, but are not limited to, blood volume, oxygen solubility in plasma and the oxygen content of a desired unit of saturated oxyhemoglobin. Preferably one or more oxygenation constants is used in the present invention to derive the selected oxygenation parameters.

From the values obtained using oxygenation constants (for example $CaO_2$, $VO_2$ and CO), the present invention solves the Fick equation $[VO_2=(CaO_2-C_vO_2) \times CO]$ by calculating the mixed venous blood oxygen content ($CvO_2$) of the patient. Once the $CvO_2$ has been determined, $SvO_2$ can be calculated and the $PvO_2$ can be readily be derived using algorithms for calculating the position of the oxyhemoglobin disassociation curve such as the Kelman equations (Kelman, *J. Appl. Physiol*, 1966, 21(4): 1375–1376; incorporated herein by reference). Similarly, other parameters such as $DO_2$, $dDO_2$ and $dDO_2/VO_2$ may be derived from the obtained values.

Using the methods disclosed herein, an anesthesiologist could continuously receive real-time data (i.e., the oxygenation parameters discussed above), thereby revealing a complete picture of the patient's global oxygenation status. Should any of the selected parameters approach the established trigger points, appropriate actions such as pharmacological intervention, fluid loading, blood transfusion or adjustment of the ventilation profile could be undertaken in plenty of time to stabilize the subject. Thus, this continuous flow of data would allow the physician to more readily determine the etiology of the oxygenation decrease (such as, but not limited to, anemia, decreased cardiac output or hypoxia) and tailor the response appropriately.

Aspects of the invention focus on the graphical display of data to users in high-risk environments (such as medicine) to reduce possible human error. In particular, the systems and displays of the invention serve to map the operator's cognitive needs into the graphical elements of the display. In certain aspects, therefore, the invention mimics body physiology so that display data better represents patient data and body function.

In one aspect, the invention utilizes task-analysis methodology to transform data into information and display oxygen-transport physiological data. The physician is able to see information (not raw data) to interpret this data - with fewer errors as compared to like interpretation of data generated by other systems - to diagnose pathological states and to take appropriate corrective action. In certain aspects, the invention thus generates a set of informative object displays from one, two or more sensors collecting data from the patient. These object displays can show, for example, (1) the relationships of data relative to other data; (2) data in context; (3) a frame of reference for the data; (4) the rate of change of information for the data; and/or (5) event information. A system constructed according to the invention is thus particularly advantageous in presenting oxygen-transport physiology to doctors.

In another aspect of the invention, the system utilizes data acquisition hardware (e.g., patient probes), a computer, and object display algorithms and software. In one preferred aspect, the software and algorithms use digital representations of analog data channels (derived, for example, from patient monitoring signals and probes) to construct a set of object displays representing oxygen-transport physiology. However, it should be noted that aspects of the invention related to the intuitive medical process diagrams of oxygen-transport physiology do not require any particular monitoring equipment. Any type of well-known patient monitoring devices could be used for gathering data that is thereafter displayed as an intuitive medical process diagram.

The invention provides several advantages over the prior art. By way of example, data displays of the invention map patient information into meaningful mental models. Doctors using such mental models are thus better able to understand complex physiology such as oxygen-transport physiology. In certain aspects, the mental models come in the form of analogies for portraying complex processes. One suitable oxygen-transport physiology model of the invention thus includes: (1) the loading of fuel in the form of oxygen onto red blood cells at the lungs; (2) the pumping of oxygenated blood by the heart to organs and tissues; (3) the unloading of oxygen from red blood cells to tissues; and (4) the utilization of the oxygen by organs and tissues. By analogy, one might compare this model to: (1) the loading of fuel in the form of coal into train box cars at a coal yard; (2) the transport of these loaded box cars by the train's locomotive to a furnace some distance away; (3) the unloading of coal from the box cars to the furnace; and (4) the burning of the coal by the furnace. In this analogy, the coal yard represents the lungs which are inflated with oxygen. The train's box cars represent the red blood cells which are loaded with oxygen. The locomotive represents the heart. And the heart pumps red blood cells carrying oxygen around a circulatory track between the lungs and the tissues. The percent of each box car's coal which is dumped at the furnace is representative of the fractional extraction of oxygen by cells within tissues. Finally, the burning coal in the furnace represents oxygen utilization by cells and tissues.

Aspects of the invention can be used in several settings. First, the system can be used with sensor sets from different manufacturers, which drive the data display. As for the display of objects, the display can be used in part, or in its entirety. Example medical domains where all or part of oxygen transport physiology can be monitored include: the intensive care unit, the operating room, the emergency room, and all procedure rooms. The display system of the invention can also be used to present oxygen-transport physiology information to the medical care team while patients are on cardiopulmonary bypass. The system can also be attached to medical simulation devices, e.g., a surgical dummy, for education and training of personnel regarding oxygen-transport physiology.

The software of the invention can be installed on medical devices currently used in data acquisition in oxygen-transport physiology. The invention can also be used to monitor oxygen-transport physiology for veterinary medicine, or to monitor oxygen-transport physiology in animal laboratories.

In certain aspects, the invention can be a module which interacts with other displays of physiology, such as respiratory physiology. It can also be used to implement research protocols which allow better execution of complex control tasks. Further use can include an interface for analyzing large data sets of oxygen-transport information.

One embodiment of the invention is a method for displaying physiologic data from a patient. In this embodiment, data is measured by way of a probe or other device from an organ in a patient. The measured data is then used to determine a physiologic quantity relating to the data, such as the blood oxygenation level in the patient. The physiologic quantity is then displayed as an object, wherein the shape of the displayed object reflects the structure of the organ.

Another embodiment of the invention is a method for displaying physiologic data from a patient. In this embodiment, the blood oxygenation levels of a patient are first measured by conventional means. A circular shape is then displayed, wherein the circular shape is shaded to represent the percentage of the patient's blood that is oxygenated.

Yet another aspect of the invention is a method for displaying physiologic data from a patient, wherein the blood oxygenation levels in a patient are first measured through conventional methods. A plurality of shapes are then a displayed on a monitor, wherein each of the plurality of shapes represents the structure of an organ in the human body.

One additional embodiment of the invention is a method for displaying physiologic data from a patient, wherein analog gauges, such as dials or needles are used to represent the physiologic data.

Another aspect of the invention is a display system for representing physiologic data from a patient. The display system includes a set of display objects, with each object representing a different, but related measurement taken from the patient. An integrated display may be formed from a set of four objects. The first object represents the patient's cardiac output, the second object represents the patient's arterial blood oxygenation levels, the third object represents the patient's venous blood oxygenation levels, and the fourth object represents the tone of the patient's arteries, capillaries and veins.

The invention is next described further in connection with preferred embodiments, and it will become apparent that various additions, subtractions, and modifications can be made by those skilled in the art without departing from the scope of the invention.

DETAILED DESCRIPTION OF THE PREFERRED EMBODIMENTS

The present invention relates to methods and systems for obtaining medical information from patients and then displaying that information in an intuitive format to a physician. The intuitive format may be termed a medical process diagram because physicians reading the displayed information can quickly perceive the importance of changing patient values. Medical process diagrams have been developed by others in non-anesthesia domains to take advantage of advancements in cognitive research.

Research in applied human factors has focused on using graphical displays in high-risk environments similar to the operating room (e.g., nuclear power control rooms and airplane flight decks) to reduce human error. The success of medical process diagrams appears to be a function of how well the semantics of the operator's cognitive needs are mapped into the graphical elements of the display. Using accepted task-analysis methods, a system was developed describing how medical doctors interpret oxygen-transport physiological data to diagnose pathological states and subsequently take appropriate corrective action in their patients. In an effort to make the many data that doctors need to interpret more informative, a set of object displays was developed.

The set of display objects was developed to illustrate: 1) the relationships of data to other data; 2) data in context; 3) a frame of reference for the data; 4) the rate of change information for the data; and 5) event information. Specifically, a system was developed for presenting oxygen-transport physiology to doctors. The system uses data acquisition hardware, a computer, oxygen transport calculation software and object display software. In one embodiment, as discussed in detail below, the object display software uses data provided by the oxygen transport calculation software to construct a set of four objects representing oxygen-transport physiology.

Unfortunately, current display systems that present physiologic data to physicians in critical care force the physicians to perform a great deal of cognitive work to interpret that data. In contrast, the display system described below utilizes visual memory cues and perceptual diagrams to map complex data graphically. These data maps are then displayed to match the mental model physicians use to interpret oxygen-transport physiology. Because the system receives analog signals from the patient and thereafter calculates several physiological quantities, patient data is used to drive the display in real-time.

I. Hardware System

Figure 1:
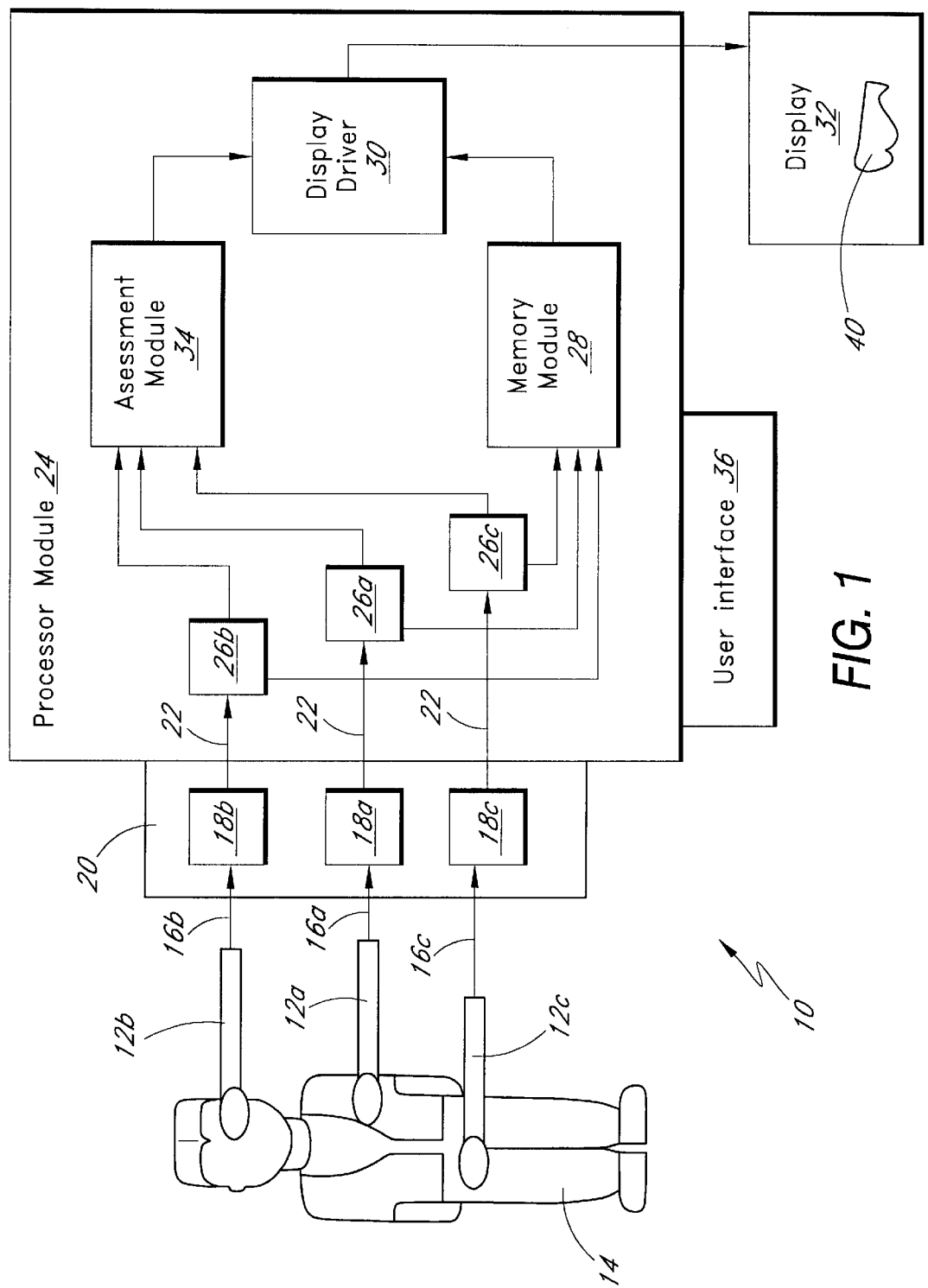
FIG. 1 is a schematic diagram illustrating one system constructed according to embodiments of the invention for collecting, processing and displaying oxygen transport physiology.

FIG. 1 illustrates a system 10 constructed according to an embodiment of the invention. A series of probes 12 are connected to various monitoring activities associated with the patient 14, e.g., a heart rate probe 12a. These probes are well known and typically generate analog signals 16 representative of the monitored activity. The signals 16 are converted through well-known A/D devices 18 in a data conversion module 20 to generate digital data corresponding to the analog signals 16. This data is made available on a data bus 22.

A processing module 24 processes data on the bus 22 to generate usable quantitative measures of patient activity as well as to compare and create object displays that, for example, (1) relate certain data relative to other data; (2) present data in context; (3) relate data to a frame of reference; (4) determine the rate of change information in the data; and/or (5) to present event information.

One embodiment of the module 24 thus includes a plurality of data processing sections 26 that analyze and/or quantify the data being input from the probe 12. For example, one section 26a, connected in the data chain to probe 12a, processes data on the bus 22 to provide a representation of heart rate in the form of a digital word. As the patient's heart rate changes, so does the digital word. A memory module 28 is used to store selected data, such as the digital word corresponding to heart rate, so that the module 24 contains a record and a current value of the patient's heart rate activity. The memory 28 also stores information, such as nominal values from which to compare data to a frame of reference, or such as extreme values representative of desired patient thresholds. The display driver section 30, connected to the sections 26, can thus command the display of the heart rate data in context on the display 32, and/or relative to frame of reference data within the memory 28.

The data from the sections 26 can also be compared to other data or related to stored thresholds within the assessment module 34. By way of example, data corresponding to probe 12a can be compared relative to probe 12b through a process of digital division within the module 34. The driver 30 can in turn command the display of this related data on the display 32. In another example, the assessment module 34 can compare other data to stored data within the memory 28; and a warning event can be displayed on the display 32 if the comparison exceed a set threshold.

Those skilled in the pertinent technology should appreciate that certain probes 12 may have self-contained A/D conversion capability and data manipulation. Furthermore, such probes can easily be connected directly to the assessment module 34 and memory 28 by known techniques.

The system 10 is controlled by inputs at a user interface 36, such as a keyboard, and the display driver 30 formats data into various object formats 40 on the display 32. Accordingly, by commanding selected processes within the assessment module 34 —such as comparison of certain data with other data - such data can be automatically displayed on the display 32 in the desired object format. The particular object formats, according to the invention, are described below. Preferably, these objects are displayed simultaneously on the same display so sufficient probes are required to collect the associated data.

Figure 2:
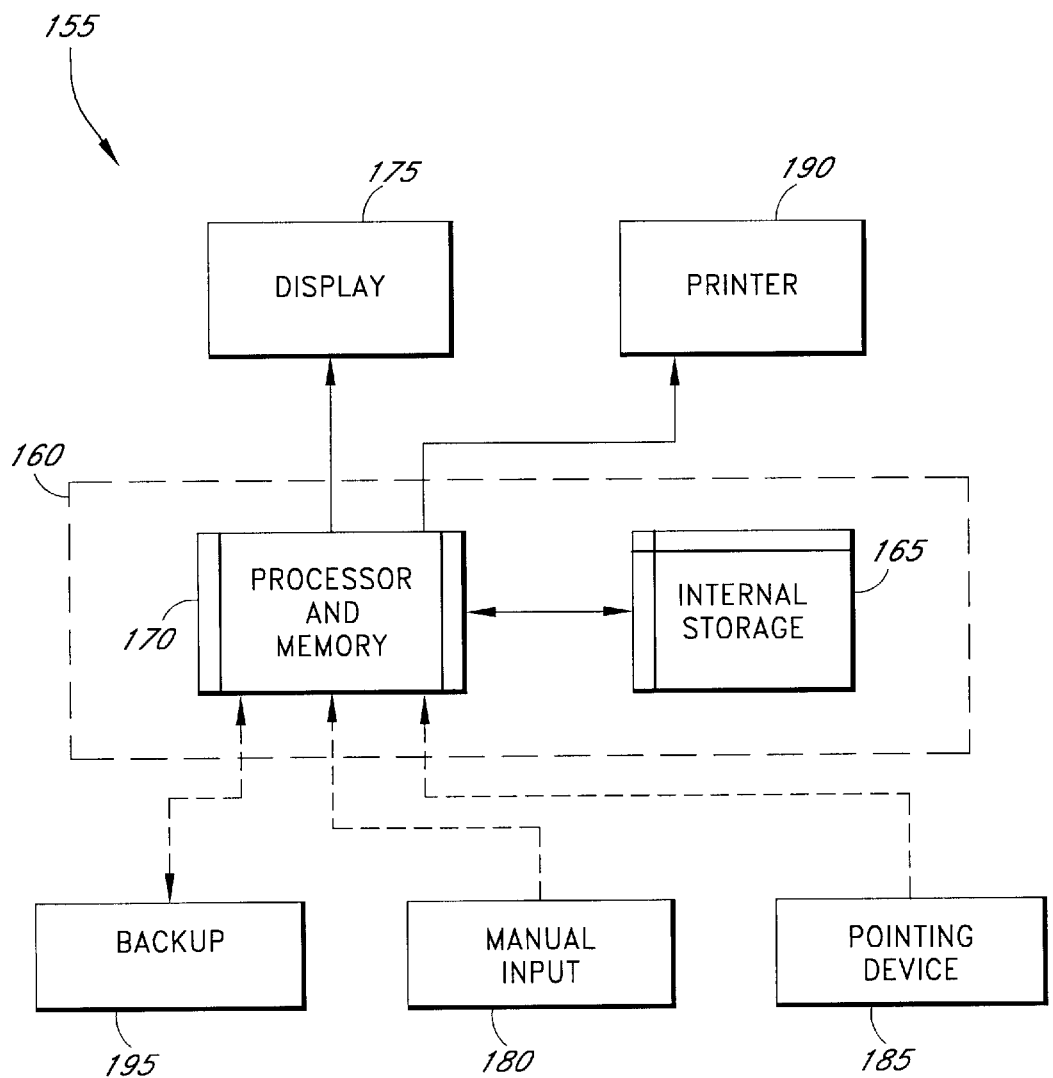
FIG. 2 is a schematic diagram of a computer system that may be used to run the present invention.

FIG. 2 shows a representative computer system 155 that may be used in conjunction with the system 10 of FIG. 1. System 155 can be operated in a stand-alone configuration or as part of a network of computer systems. The system 155 is an integrated system that collects data from the patient and presents processed data to a display for viewing by a physician.

The computer system 155 includes blood-monitoring software executed in conjunction with an operating system, for instance Windows 95 available from Microsoft Corporation, on a computer 160. Other embodiments may use a different operational environment or a different computer or both.

In an alternate embodiment of the invention, the computer 160 can be connected via a wide area network (WAN) connection to other physicians or hospitals. A WAN connection to other medical institutions enables a real-time review of the patient's progress during surgery or in the intensive care unit.

Referring again to FIG. 2, one embodiment of the computer 160 includes an Intel Pentium or similar microprocessor running at 300 MHz and 32 Megabytes (Mb) of RAM memory (not shown). The system 155 includes a storage device 165, such as a hard disk drive connected to the processor 170. The hard drive 165 is optional in a network configuration, i.e., the workstation uses a hard disk or other storage device in a file server. If the computer 160 is used in the stand-alone configuration, the hard drive 165 is preferably 100 Mb or more. However, the system is not limited to particular types of computer equipment. Any computer equipment that can run the display system described herein is anticipated to function within the scope of this invention.

The computer 160 is integrated with a group of computer peripherals, and is connected to a VGA (video graphics array) display standard, or better, color video monitor, which provides the display output of the system 155. The display 175 may be a 17 inch monitor running at 1024×768 pixels with 65,536 colors. A keyboard 180 that is compatible with IBM AT type computers may be connected to the computer 160. A pointing device 185, such as a two or three button mouse can also connect to the computer 160. Reference to use of the mouse is not meant to preclude use of another type of pointing device.

A printer 190 may be connected to provide a way to produce hard-copy output, such as printouts for file records. In one configuration, a backup device 195, such as a Jumbo 250 Mb cartridge tape back-up unit, available from Colorado Memory Systems, is preferably connected to the computer 160.

In an alternate embodiment of a stand-alone configuration, or as one of the workstations of a network configuration, the system 155 may include a portable computer, such as a laptop or notebook computer, e.g., a Premium Executive 386SX/20, available from AST Research, or other computers available from a variety of vendors. The portable computer (not shown) is equipped with components similar to that described in conjunction with computer 160.

It will be understood by one skilled in the technology that a programmed computer can also be implemented completely or partially with custom circuitry. Therefore, the chosen implementation should not be considered restrictive in any matter.

II. Software

Many different ways of implementing the software of the present invention will be known to skilled technologists. For example, programming languages such as Labview, C++, Basic, Cobol, Fortran or Modula-2 can be used to integrate the features of the present invention into one software package. An alternative method of illustrating the software of the present invention is to use a spreadsheet program to collect and determine the $PvO_2$ of a patient in real-time. This method is described in detail below.

A. Determining Blood Gas Levels

Figure 3:
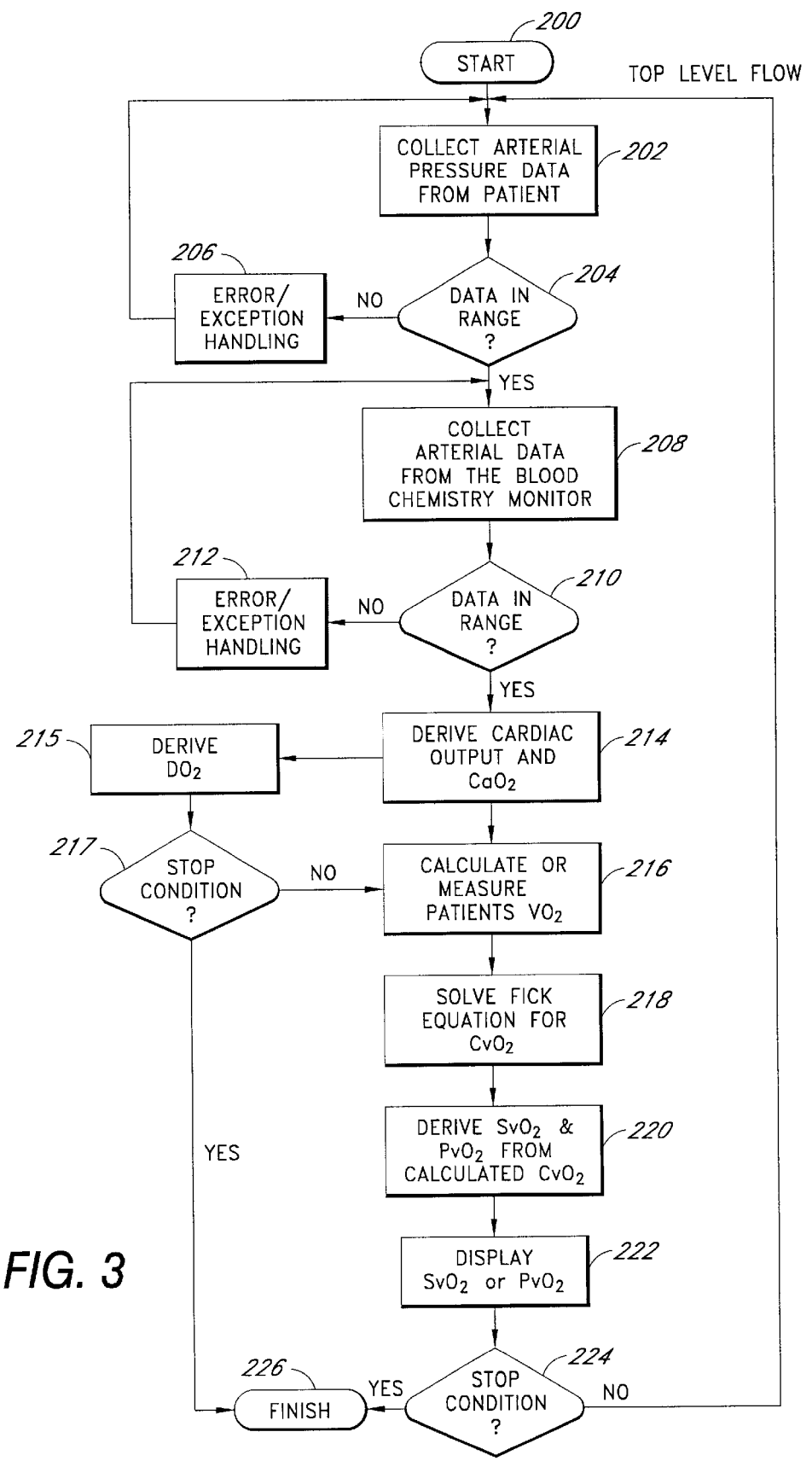
FIG. 3 is a flowchart detailing a preferred software scheme that may be used to run the present invention.

As discussed above, the systems and methods of the present invention collect data from a patient and determine various tissue oxygenation parameters of a patient in real-time. Software is used to direct this process. Those skilled in the art will appreciate that the desired parameters may be derived and displayed using various software structures written in any one of a number of languages. FIG. 3 illustrates one possible software scheme that could be used in conjunction with the disclosed methods and systems.

Referring now to FIG. 3, the process is begun when a start signal is transmitted by the user to the system at start state 200. The start signal can be a keystroke of mouse command that initiates the software to begin collecting data. After receiving the start command at state 200, arterial pressure data is collected from a patient at state 202. Arterial pressure data may be collected by hooking a patient up to an arterial pressure monitor as is well known.

Once data have been collected from a patient at state 202, a "data in range" decision is made at decision state 204. At this stage, the software compares the data collected at state 200 with known appropriate ranges for arterial pressure values. Appropriate ranges for arterial pressure data are, for example, between 70/40 and 250/140.

If data collected at process state 200 are not within the range programmed in decision state 204, or if the arterial pressure wave is abnormal an error/exception handling routine is begun at state 206. The error handling routine at state 206 loops the software back to process state 200 to re-collect the arterial pressure data. In this manner, false arterial pressure data readings will not be passed to the rest of the program. If the data collected at process state 200 are in the appropriate range at decision state 204, the software pointer moves to process state 208 that contains instructions for collecting arterial data. Preferably the collected data will include patient temperature, arterial pH, hemoglobin levels, $PaO_2$ and $PaCO_2$. Moreover, the data is preferably generated by an attached blood chemistry monitor which may provide information on the patient's blood gas levels, acid-base status and hematology status. In such embodiments the data is collected by receiving data streams via the serial connection from the blood chemistry monitor into the computer. Alternatively, the relevant values may be obtained from accessing data that is manually input from the keyboard.

As described previously, the blood chemistry monitor continually samples arterial blood from the patient preferably determining several properties of the patient's blood from each sample. Data corresponding to each of the properties taken from the blood chemistry monitor at process state 208 are checked so that they are in range at decision state 210. An appropriate range for the pH is 7.15 to 7.65. An appropriate range for the hemoglobin level is from 0 to 16 g/dL. An appropriate range for the $PaO_2$ is from 50 mm Hg to 650 mm Hg while an appropriate range for the $PCO_2$ is from 15 mm Hg to 75 mm Hg.

If data are not within the appropriate ranges for each specific variable at decision state 210, an error/exception handling routine at state 212 is begun. The error/exception handling routine at state 212 independently analyzes variables collected at state 208 to determine whether it is in range. If selected variables collected at state 208 are not within the appropriate range, the error/exception handling routine 212 loops a software pointer back to state 208 so that accurate data can be collected. If the selected data are in range at decision box 210, the software then derives the $CaO_2$ value along with the cardiac output (CO) from the previously obtained arterial pressure data at state 214.

As discussed, cardiac output can be derived from arterial pressure measurements by any number of methods. For example, the Modelflow system from TNO Biomedical can derive a cardiac output value in real-time from an arterial pressure signal. Other methods, as discussed above, could also be used at process step 214 to determine cardiac output. Once a cardiac output value has been determined at process step 214, the patient's total oxygen transport ($DO_2$) may be derived at process step 215. As previously discussed the total oxygen transport is the product of the cardiac output and the arterial blood oxygen content. This parameter may optionally be displayed and, as indicated by decision state 217, the program terminated if the software has received a stop command. However, if the software has not received a keyboard or mouse input to stop collecting data at decision state 217, a pointer directs the program to process state 216 to derive further parameters. Specifically, process state 216 relates to the measurement or input of the patient's $VO_2$.

The patient's $VO_2$ can be calculated using the methods previously described measured by hooking the patient up to a suitable ventilator and measuring his oxygen uptake through a system such as the Physioflex discussed above or using a number of other devices such as systems manufactured by Sensormedics and Puritan Bennett. By determining the amount of oxygen inspired and expired, the ventilator may be used to calculate the total amount of oxygen absorbed by the patient. After the patient's $VO_2$ value has been determined at process step 216, these variables are applied to the Fick equation at state 218 to provide a real time $CvO_2$. The Fick equation is provided above.

Once the $CvO_2$ is known, mixed venous oxyhemoglobin saturation ($SvO_2$) and the mixed venous oxygen tension ($PvO_2$) can be derived at state 220. As previously explained, values for mixed venous pH and $PCO_2$ are assumed to have a constant (but alterable) relation to arterial pH and $PaCO_2$ respectively and these are used, along with other variables, in the Kelman equations to define the position of the oxyhemoglobin dissociation curve. Alternatively, algorithms can be derived to calculate these values. Knowing the Hb concentration, a $PvO2$ is derived that then provides a total $CvO_2$ (which includes contributions from Hb, plasma and PFC) equal to the $CvO_2$ determined from the Fick equation. If the $CvO_2$ value will not "fit" the Fick equation, another $PvO_2$ value is chosen. This process is repeated until the Fick equation balances and the true $PvO_2$ is known.

Those skilled in the art will appreciate that the same equations and algorithms may be used to derive, and optionally display, the mixed venous blood oxyhemoglobin saturation $SvO_2$. That is, $SvO_2$ is closely related to $PvO_2$ and may easily be derived from the oxygen-hemoglobin dissociation curve using conventional techniques. It will further be appreciated that, as with $PvO_2$, $SvO_2$ may be used to monitor the patient's oxygenation state and as an intervention trigger if so desired by the clinician. As discussed above, mixed venous blood oxyhemoglobin saturation may be used alone in this capacity or, more preferably, in concert with the other derived parameters.

After deriving values for $PvO_2$, $SvO_2$ or both, the value or values may be displayed on the computer display at step 222. If the software has not received a keyboard or mouse input to stop collecting data at decision state 224, a pointer loops the program back to process state 200 to begin collecting arterial pressure data again. In this manner, a real-time data loop continues so that the patient's mixed venous blood oxygen tension ($PvO_2$) or saturation ($SvO_2$) is constantly updated and displayed on the computer at state 222. If the software has received a stop command from a keyboard or mouse input at decision state 224, then a finish routine 226 is begun.

B. Calculating Oxygen Transport Values

The following system utilizes a large Microsoft EXCEL® spreadsheet to collect information from the patient and display the desired parameters including $PvO_2$, $SvO_2$ and $DO_2$. Before receiving real-time inputs of cardiovascular and oxygenation variables, a number of oxygenation constants may be entered into the system. These constants preferably include the patient's estimated blood volume, oxygen solubility in plasma and the oxygen content of 1 g of saturated oxyhemoglobin. The oxygenation constants are then stored in the computer's memory for use in later calculations.

TABLE 1 shows commands from part of a Microsoft EXCEL® spreadsheet that collects a patient's data and derives the value of the desired oxygenation parameters. The program is initialized by assigning names to various oxygenation constants that are to be used throughout the software. In the embodiment shown, oxygenation constants corresponding to blood volume (BV), oxygen solubility in a perfluorocarbon emulsion (O2SOL), specific gravity of any perfluorocarbon emulsion (SGPFOB), intravascular half-life of a perfluorocarbon emulsion (HL), weight/volume of a perfluorocarbon emulsion (CONC), barometric pressure at sea level (BARO), milliliters oxygen per gram of saturated hemoglobin (HbO) and milliliters of oxygen per 100 ml plasma per 100 mm of mercury (PIO) are all entered. The constants relating to perfluorocarbons would be entered in the event that fluorocarbon blood substitutes were going to be administered to the patient.

An example of starting values for Kelman constants, a subset of the oxygenation constants, is also shown in TABLE 1. These starting values are used in later calculations to derive the patient's mixed venous oxygenation state or other desired parameters such as mixed venous blood oxyhemoglobin saturation. As with the other oxygenation constants the Kelman constants are also assigned names as shown in TABLE 1.

TABLE 1

| ASSUMPTIONS: | VALUES AT START: |
| --- | --- |
| Blood Volume (ml/kg) -BV | 70 |
| $O_2$ solubility in PFB (ml/dl @ 37 deg C) O2SOL | 52.7 |
| Specific Gravity of PFOB -SGPFOB | 1.92 |
| Intravascular half-life of Oxygent HT (hours) -HL | = 1/2 Life of Oxygent |
| Wgt/vol of PFOB emulsion/100 -CONC | 0.6 |
| Barometric Pressure @ sea level -BARO | 760 |
| MI O2 per gram saturated Hb -HbO | 1.34 |
| MI O2 per 100 ml plasma per 100 mm Hg -HIO | 0.3 |
| KELMAN CONSTANTS: | VALUES AT START |
| Ka1 | = −8.5322289*1000 |
| Ka2 | = 2.121401*1000 |
| Ka3 | = −6.7073989*10 |
| Ka4 | = 9.3596087*100000 |
| Ka5 | = −3.1346258*10000 |
| Ka6 | = 2.3961674*1000 |
| Ka7 | −67.104406 |

Figure 4:
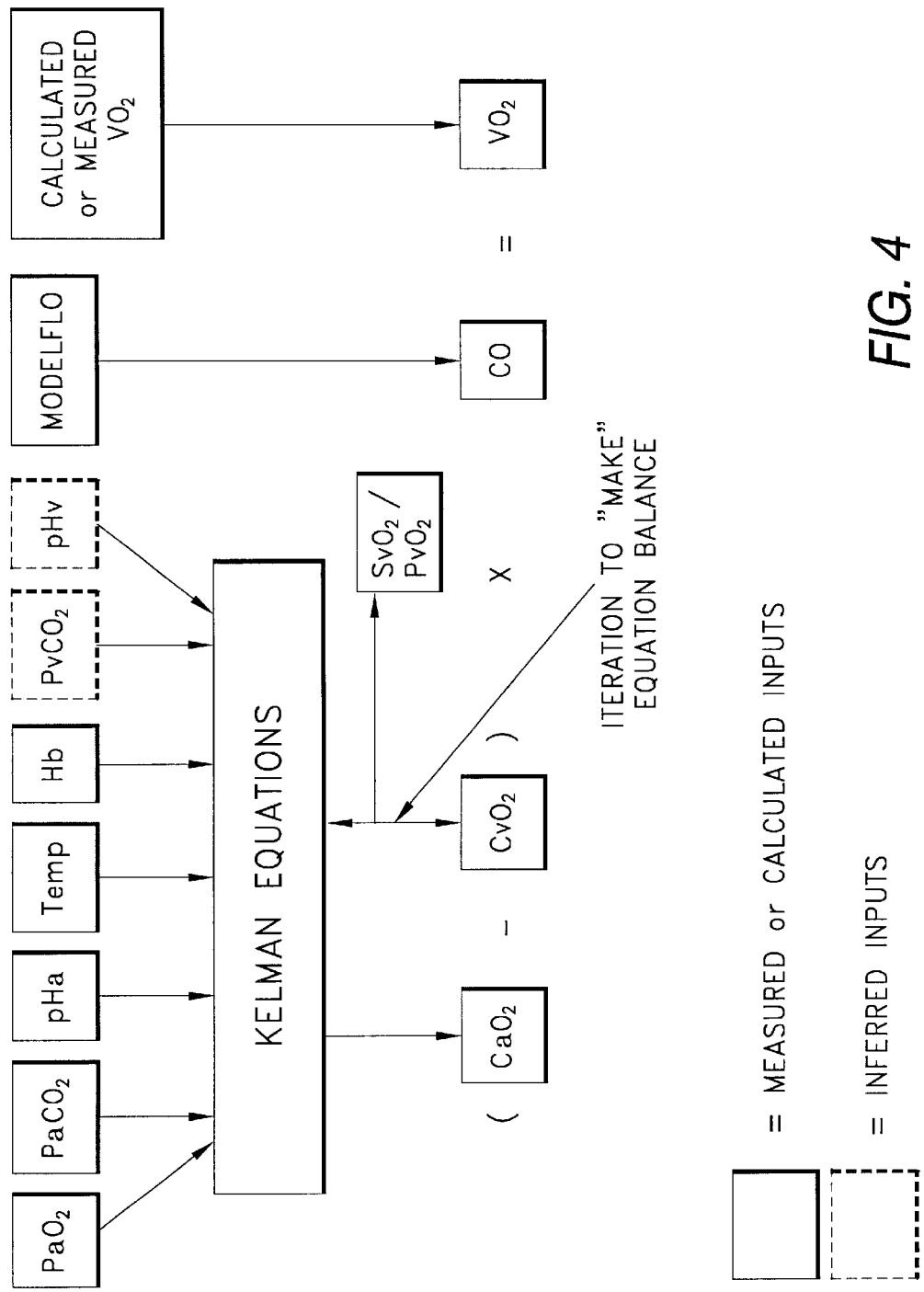
FIG. 4 is a schematic diagram of data input and calculations as performed in selected embodiments of the present invention.

After the oxygenation constants, including the Kelman constants, have been assigned names, real time inputs from the arterial pressure lines and blood chemistry monitor may be initialized and begin providing data. As shown in TABLE 2, the system depicted in this embodiment derives or receives data relating to the arterial oxyhemoglobin saturation percentage ($SaO_2$). In particular, saturation percentages are derived from arterial data for oxygen tension ($PaO_2$), pH (pHa), carbon dioxide tension ($PaCO_2$) and body temperature (TEMP). If desired by the clinician, the present invention provides for the real-time display of $SvO_2$ values (as derived from calculated $PvO_2$, pHv, $PvCO_2$ and temperature) to be used for the monitoring of the patient's tissue oxygenation status. As previously discussed, values for $PvCO_2$ and pHv are related, by a fixed amount, to those of $PaCO_2$ and pHa respectively as determined by algorithms. Cardiac output (CO) is also input as is $VO_2$. FIG. 4 provides a schematic representation of this procedure and resulting data.

When Hb concentration, arterial blood gas and acid/base parameters are entered (automatically or manually) into the program, the $O_2$ delivery and consumption variables for both red cell containing Hb and for the plasma phase may be determined. Those variables relating to PFC (in the case of blood substitutes) or Hb based oxygen carrier can also be determined.

Referring again to FIG. 4, numerical values useful for the calculation of $CaO_2$ relate to Hb concentration, arterial oxygen tension ($PaO_2$), arterial carbon dioxide tension ($PaCO_2$), arterial pH (pHa) and body temperature. The position of the oxygen-hemoglobin dissociation curve is calculated using the Kelman equations, which are input as oxygenation constants in the program. These calculations produce a curve that, over the physiological range of $O_2$ tensions, is indistinguishable from the parent curve proposed by Severinghaus (*J. Appl. Physiol.* 1966, 21: 1108–1116) incorporated herein by reference. As shown schematically in FIG. 4, iteration may be used to calculate a $PvO_2$ (via $SvO_2$) that results in the required mixed venous oxygen contents in Hb, plasma and fluorocarbon to satisfy the Fick equation.

TABLE 2

| INPUTS: | AT START: |
| --- | --- |
| Hemoglobin (Gm/dl) -Hb | 6 |
| Arterial Oxyhemoglobin saturation (%) -SaO2 | |
| Calculated Arterial Oxyhemoglobin saturation (%) -SaO2CALC | = 100*(SPaO2*(SPaO2*(SPaO2*(SPaO2 + Ka3) + Ka2) + Ka1))/(SPaO2*(SPaO2 + Ka7) + Ka6) + Ka5) + K |
| Active Input Value for SvO2 -SaO2USED | = IF(SaO2<>O,SaO2,SaO2CALC) |
| Mixed venous blood oxyhemoglobin saturation (%) -SvO2 | |
| Calculated Mixed venous blood oxyhemoglobin saturation - | = 100*(SPvO2*(SPvO2*(SPvO2*(SPvO2 + Ka3) + Ka2) + Ka1))/(SPaO2*(SPaO2 + Ka7) + Ka6) + Ka5) + K |
| SVO2CALC | |
| Active Input Value for SvO2 -SvO2USED | = IF(SvO2<>O,SvO2,SvO2CALC) |
| Arterial Oxygen Partial Pressure (mm Hg) -PaO2 | 100 |
| Calculated 'standardized' PaO2 -SPaO2 | = PaO2*10((0.024*(37-TEMPUSED)) + (0.4*(pHaUSED.7.4)) + (0.06*(LOG10(40)-LOG10(PaCO2USED)))) |
| Active Input Value for PaSO2 -PaSO2USED | = IF(PaO2<>O,PaO2,SPaO2) |
| Arterial pH -pHa | |
| Normal Arterial pH -pHaNORM | 7.4 |
| Active Input Arterial pH -pHaUSED | = IF(pHa<>O,pHa,pHaNORM) |
| Arterial PCO2 -PaCO2 | |
| Norma) PaCO2 -PaCO2NORM | 40 |
| Active Input Arterial PCO2 -PaCO2USED | = IF(PaCO2<>,PaCO2,PaCO2NORM) |
| Body Temp C -TEMP | |
| Normal Body Temp C -TEMPNORM | 37 |

TABLE 2-continued

| INPUTS: | AT START: |
|---|---|
| Active Input Body Temp C -TEMPUSED | = IF(TEMP<>O,TEMP,TEMPNORM) |
| Mixed Venous Oxygen Partial Pressure (mm Hg) -PvO2 | 40.6819722973629 |
| Calculated 'standardized' PvO2 -SPvO2 | = PvO2*10*((0.024*(37-TEMPUSED)) + (0.4*(pHvUSED-7.4)) + (0.06*(LOG10(40)-LOG10(PvCO2USED)))) |
| Mixed Venous pH pHv | |
| Normal Venous pH | 7.4 |
| Active Input Mixed Venous pH -pHvUSED | = IF(pHv<>O,pHv,pHvNORM) |
| Mixed Venous PCO2 -PvCO2 | |
| Normal Mixed Venous PCO2 -PvCO2NORM | 40 |
| Active Input Mixed Venous PCO2 -PvCO2USED | = IF(PvCO2<>O,PvCO2NORM) |
| Cardiac Output (I/mm) -CO | = ((14-Hemoglobin (gm/dl) * CO Response to 1 gram of Hb Depletion) + 5 |
| CO Response to 1 gr Hb depletion -COCHG | 0.7 |
| Intravascular Oxygent HT Dose(ml/kg) -PFB | |
| Time Adj. Intravascular Oxygent HT Conc(ml/kg) -TAPFB | |
| Patient's Weight (kg) -kg | 70 |
| Total O2 Consumption (ml/min/kg) -VO2KG | 3 |
| Calculated Blood Volume (ml) -CBV | -BV*kg |
| Calc input Total O2 Consumption (ml/min/kg) -VO2 | -kg*VO2KG |

TABLE 3

| DESCRIPTION: | CALCULATIONS: |
|---|---|
| Arterial O2 Content in Hemoglobin (ml/dl) -CaO2Hb | = ((Hb*HbO*SaO2USED)/100) |
| Arterial O2 Content in Plasma (ml/dl) -CaO2PI | = ((PaO2*PIO)/100) |
| Arterial O2 Content in PFB (ml/dl) -CaO2PFB | = ((PFB*kg*CONC)/SGPFOB)/(kg*BV*0.01)* ((O2SOL*PaO2)/(100*BARO)) |
| Arterial Oxygen Content (ml/dl) -CaO2 | = (CaO2Hb + CaO2PI + CaO2PFB) |
| Mixed Venous O2 Content in Hemoglobin (ml/dl) -CvO2Hb | = ((Hb*HbO*SvO2USED)/100) |
| Mixed Venous O2 Content in Plasma (ml/dl) -CvO2PI | = ((PvO2*PIO)/100) |
| Mixed Venous O2 Content in PFB (ml/dl) -CvO2PFB | = ((PFB*kg*CONC)/SGPFOB)/(kg*BV*0.01)* ((O2SOL*PvO2)/(100*BARO)) |
| Mixed Venous Oxygen Content (ml/dl) -CvO2SUM | = (CvO2Hb + CvO2PI + CvO2PFB) |
| Mixed Venous Oxygen Content (ml/dl) -CvO2 | = IF(CVO2SUM>O,(CVO2SUM),CvO2CALC2) |
| Mixed Venous O2 Content (ml/dl) -CvO2CALC2 | = CaO2-VO2/(CO*10)) |
| Percent of VO2 provided from plasma | = ($O_2$ Used From Plasma/Active Input Total $O_2$ Consumption)*100 |
| Percent VO2 provided by PFB | = 100*($O_2$ Used From Perflubron/Active Input Total $O_2$ Consumption) |
| Percent of VO2 provided by plasma and PFB | = 100*(($O_2$ Used From Plasma + $O_2$ Used From Perflubron/Active Input Total $O_2$ Consumption)*100 |

TABLE 4

| DESCRIPTION: | OUTPUTS |
|---|---|
| Total Oxygen Transport (ml/min) -TDO2 | = CaO2*CO*10 |
| O2 Transport in Hemoglobin (ml/min) -DO2Hb | = (CaO2Hb)*CO*10 |
| O2 Transport in plasma (ml/min) -DO2PI | = CaO2PI*CO*10 |
| O2 Transport in Perflubron (ml/min) -DO2PFB | = CaO2PFB*CO*10 |
| Calc Total O2 Consumption (ml/min) -VO2CALC | = (CaO2-CvO2)*CO*10 |
| Active Input Total O2 Consumption (ml/min) -VO2USED | = IF(VO2<>O, VO2, VO2CALC) |
| Oxygen Used from Hemoglobin (ml/min) -VO2Hb | = (CaO2Hb-CvO2Hb)*CO*10 |
| Oxygen Used from plasma (ml/min) -VO2PI | = (CaO2PI-CvO2PI)*(CO*10) |
| Oxygen Used from Perflubron (ml/min) -VO2PFB | = (CaO2PFB-CvO2PFB)*(CO*10) |
| Total Oxygen Extraction Coefficient -OEC | = (CaO2-CvO2)/CaO2 |
| Hemoglobin Oxygen Extraction Coefficient -HOEC | = (SaO2USED-SvO2USED)/SaO2USED |

Based on the numerical values provided, the program calculates oxygenation parameters such as $PvO_2$ and $SvO_2$ in real time, as shown in TABLE 2. These values are then fed into the display system described below to generate perceptual diagrams. These diagrams are then used by the physician to determine, for example, when to give the patient a blood transfusion or alter the patient's clinical management. Significantly, the displayed values may be used to monitor the physiological effects of blood substitutes, including those based on hemoglobin or perflurochemicals following their administration.

TABLE 3 and TABLE 4 show additional information that may be provided by the instant invention further demonstrating its utility and adaptability. More specifically, TABLE 3 provides various oxygenation values that may be calculated using the methods disclosed herein while TABLE 4 provides other indices of oxygen consumption and oxygen delivery that are useful in optimizing patient treatment.

A closer examination of TABLE 3 shows that the system of the present invention may be used to provide the individual oxygen content of different constituents in a mixed oxygen carrying system. In particular, TABLE 3 provides calculations that give the arterial or venous oxygen content of circulating hemoglobin, plasma and fluorochemical respectively. Such values would be of particular use when intravenously introducing fluorochemical emulsion blood substitutes in conjunction with surgical procedures.

TABLE 4 illustrates that the present invention may also be used to provide real-time information regarding oxygen consumption and delivery. As mentioned previously, Hb or Hct measurements are not a suitable reflection of tissue oxygenation. This is mainly because they only give an indication of the potential arterial $O_2$ content ($CaO_2$), without providing information about the total oxygen transport ($DO_2$) to the tissues where it is to be used. However as seen in TABLE 4 the instant invention solves this problem by providing on line oxygen transport information which is derived based on $CaO_2$ and cardiac output (CO).

Currently cardiac output is measured using thermodilution, and $CaO_2$ is calculated typically by measuring the arterial oxyhemoglobin saturation ($SaO_2$) and hemoglobin levels, and inserting these values into the following equation: $CaO_2 = ([Hb] \times 1.34 \times SaO_2) + (PaO_2 \times 0.003)$, where [Hb] = hemoglobin concentration (in g/dL); 1.34 = the amount of oxygen carried per gram of fully saturated hemoglobin; $PaO_2$ = the arterial oxygen tension; and 0.003 is the amount of oxygen carried by the plasma (per deciliter per mm Hg of oxygen tension).

The present invention combines the continuous cardiac output algorithm with the Kelman equations to provide the position of the oxygen hemoglobin dissociation curve. Using on-line and off-line inputs of body temperature, hemoglobin, and arterial blood gases, the present invention is able to trend $DO_2$ on a continuous basis. The factors used to determine $DO_2$ are displayed along with their product; thus, the etiology of a decrease in $DO_2$ (inadequate cardiac output, anemia, or hypoxia) would be readily apparent to the physician, decisions regarding the appropriate interventions could be made expeditiously, and the results of treatment would be evident and easily followed.

More particularly, preferred embodiments of the invention may be used to provide and display real-time $DO_2$, arterial blood gases, hemoglobin concentration and CO (and all other hemodynamic data already discussed such as BP, heart rate, systemic vascular resistance, rate pressure product and cardiac work). As shown in TABLE 3, such embodiments can also provide separate readouts of contributions of Hb, plasma and PFC (if in circulation) to $DO_2$. That is, the oxygen contributions of each component may be accurately monitored and adjusted throughout any therapeutic regimen. Such data would be particularly useful in both the OR and ICU for providing a safety cushion with respect to the oxygenation of the patient.

The importance of maximizing $DO_2$ for certain patients in the ICU has been underscored by recent studies. The present invention may also be used for determining when such intervention is indicated and to provide the data necessary for achieving the desired results. Once $DO_2$ is known it is possible to calculate the maximum $O_2$ consumption ($VO_2$) that could be supported for a certain chosen (and alterable) $PvO_2$. As previously discussed, this value may be termed deliverable oxygen ($dDO_2$). For instance, a $PvO_2$ of 36 mm Hg might be chosen for a healthy 25 year old patient, whereas a $PvO_2$ of 42 mm Hg or higher might be needed for an older patient with widespread arteriosclerosis or evidence of coronary atheroma or myocardial ischemia. Oxygen consumption under anesthesia is variable, but almost always lies in the range of 1.5 to 2.5 ml/kg/min. If the supportable $VO_2$, at the chosen $PvO_2$, was well above this range all would be well and no intervention would be necessary. The closer the supportable $VO_2$ to the normal $VO_2$ range the earlier intervention could be considered.

This relationship could be used to provide a single value, based on deliverable oxygen ($dDO_2$) vs. oxygen consumption ($VO_2$), that would simplify patient care. As previously explained, $dDO_2$ is the amount of oxygen transported to the tissue that is able to be delivered before the partial venous oxygen pressure ($PvO_2$) and, by implication, tissue oxygenation tension falls below a defined level. Thus, if it is desired that the $PvO_2$ value not fall below 40 (this number is variable for different patients depending on their general medical condition) then $DO_2$ (and by implication $dDO_2$) must be maintained at sufficient levels.

The supply/demand ratio ($dDO_2/VO_2$) for a selected $PvO_2$ can be used to provide a single value showing that the amount of oxygen being administered is sufficient to maintain the desired oxygenation state. For example, if it is known that the $dDO_2$ required to maintain a $PvO_2$ of 40 is, say, 300 ml/min and the measured ($VO_2$) is 200 ml/min then the patient is being supplied with enough oxygen for his needs. That is, the supply/demand ratio is 300 ml/min÷200 ml/min or 1.5. A supply/demand ratio of 1 would imply that the $PvO_2$ (or other selected parameter i.e. $SvO_2$) was at the selected trigger value (here 40 mm Hg). Conversely, if the $dDO_2$ (deliverable oxygen) is 200 ml/min and the $VO_2$ (oxygen consumption) is 300 ml/min then the ratio is 0.66 and the patient is not receiving sufficient oxygen (i.e., the $PvO_2$ will be less than 40). Continuous monitoring and display of this ratio will allow the clinician to observe the value approaching unity and intervene appropriately.

III. Displaying Objects Related to the Oxygen Transport Values

As discussed above, the computer system 155 of FIG. 2 includes software and systems for displaying medical process diagrams relating the values calculated above.

The display system collects the oxygen transport values and creates display objects that are presented to the physician. Although some of the data may be derived by reading raw analog or digital data from a patient monitor, many of the values may be read from calculated data such as shown in TABLES 1–4 above.

The system might sample the data at 200 times per second, and update the display every 2 seconds. However, the system may be capable of higher sampling and display updates to provide the most up to date data to the physician.

As discussed above, the perceptual diagrams comprise a series of data objects representing physiological processes in the body. Examples of these data objects include a red blood cell object, a heart pump object, a vascular resistor object and a metabolism object. These objects, as discussed below, can be displayed alone or together to provide a perceptual diagram of an oxygen transport system in a patient.

A. The Red Blood Cell Object

Figure 5:
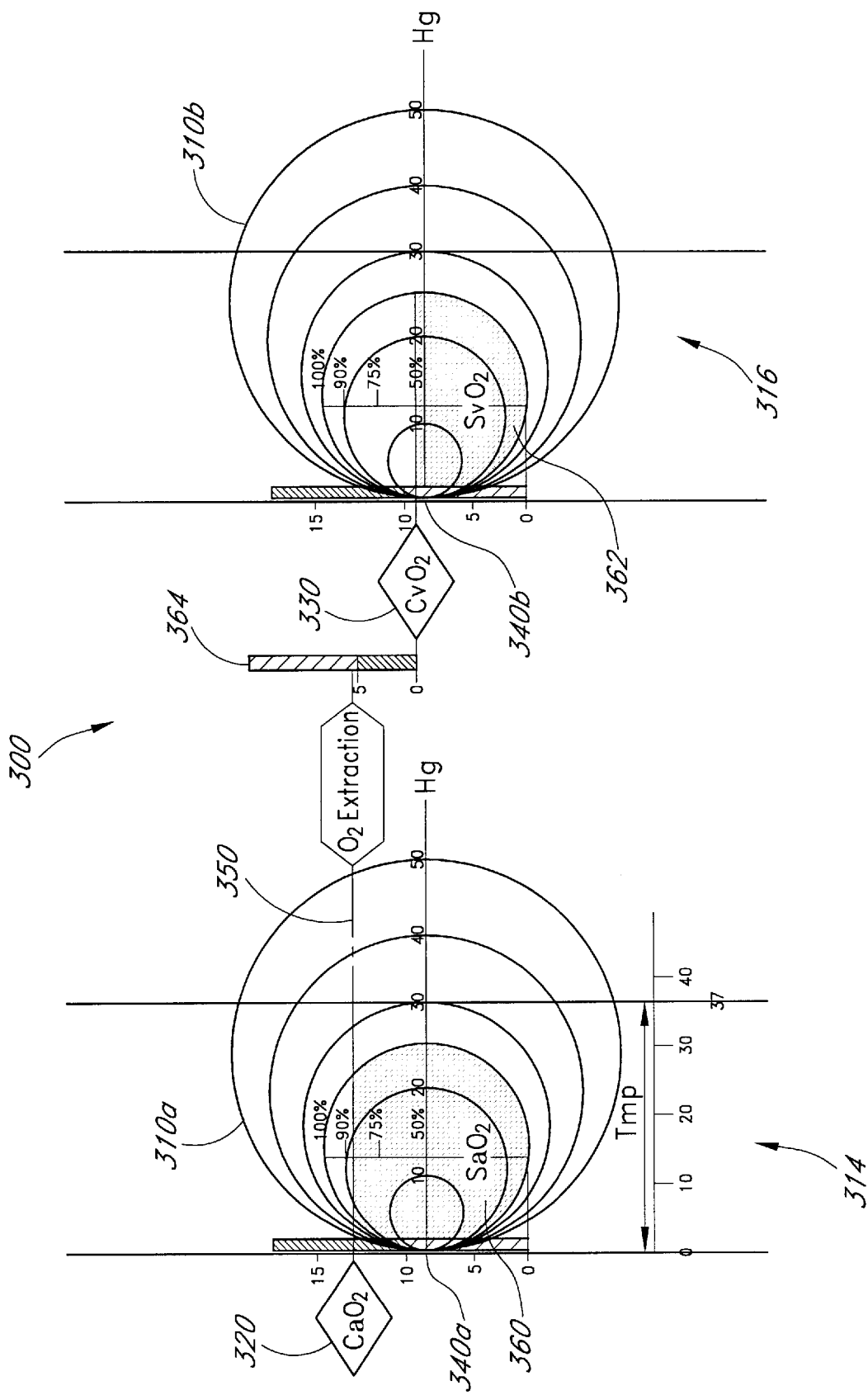
FIG. 5 illustrates one embodiment of a red blood cell object.

Referring to FIG. 5, a red blood cell object 300 displays information relating to the amount of hemoglobin in a patient's blood, the amount of oxygen which is loaded onto the red blood cells, the effect of temperature on blood viscosity, and the oxygen content of the blood. In one aspect, this relationship can be formulated by the following equation: Arterial Oxygen Content =(Arterial Oxygen Saturation)×(Hemoglobin)×(1.34). In FIG. 5, Arterial Oxygen Saturation is labeled "$SaO_2$", hemoglobin is labeled as "HB", and Arterial Oxygen Content is labeled as "$CaO_2$".

These red-blood cell related values are then converted to a perceptual diagram (e.g., on a computer display 32, FIG. 1) in the form of a pair of nonconcentric circle sets 310a, 310b. As indicated in FIG. 5, there is an arterial portion 314 and venous portion 316 of the red blood cell object 300. In the arterial portion 314, the patient's $CaO_2$ value is indicated by a diamond 320 and is mapped to the Y-axis. The patient's hemoglobin level, the volume percentage of erythrocytes in whole blood, is mapped to the X-axis. In the venous portion 316, the patient's $CvO_2$ is indicated by a diamond 330 and is mapped to the Y-axis. The hemoglobin level is mapped to the X-axis.

The nonconcentric circles 310a,b are created by using a Y-axis to define a tangential line along the left-most point 340a,b of the nonconcentric circles 310a,b. Each nonconcentric circle includes the same left-most point 340a,b along the Y-axis.

As the level of arterial oxygen increases, the $CaO_2$ diamond 320 moves upward along the Y-axis. A horizontal oxygen extraction line 350 indicates the level of arterial oxygenation by defining the upper boundary of a shaded area 360 in the arterial red-cell shaped object 310a. The red cell objects 310a,b can be partially or completely shaded, as illustrated in FIG. 5 to show the percent filled with oxygen of the patient's red blood cells (e.g., when half shaded, the cell is only half filled with oxygen). As the level of hemoglobin (Hb) in the patient increases, the shading is with respect to an increased circumference circle of the red-cell shaped object 310a,b also increases.

Similarly for the venous red cell shaped object 310b, as the level venous oxygenation rises and falls in the patient, the $CvO_2$ diamond 330 moves up and down along its Y-axis. As the $CvO_2$ diamond 330 moves up and down, the amount of shading 370 within the venous red-cell shaped object 310b changes. Thus, the oxygenation on the venous side of the vascular circuit is readily illustrated to the physician. When the arterial and venous oxygen contents are compared by looking at the relative shading 360 (arterial side) and 362 (venous side), a rapid, perceptual understanding of oxygen extraction is made evident. As is known, Oxygen Extraction =(Arterial Oxygen Content)-(Venous Oxygen Content). Thus by comparing the relative shading of the red-cell shaped objects 310a and 310b, a physician can perceptually understand the amount of oxygenation extraction in the patient.

The oxygen extraction line 350 is extended from the arterial blood cell 310a to an oxygen extraction sliding scale 364. In turn, the oxygen extraction sliding scale 364 maintains the $CvO_2$ diamond 330 as its lower boundary. As the level of $CaO_2$ rises, the oxygen extraction sliding scale 364 increases. Similarly, as the level of $CvO_2$ drops, the oxygen extraction sliding scale 364 also increases. This makes sense since the amount of oxygen extraction is expected to increase with rising arterial oxygen pressure or with decreasing venous oxygen pressure. A physician can thereby look to the oxygen extraction sliding scale 364 as a quick measure of the amount of oxygen extraction taking place in the patient. The manner in which the red-cell object 300 mimics the in vivo action of actual red blood cells makes the red-cell object 300 very intuitive to a physician.

Figure 6:
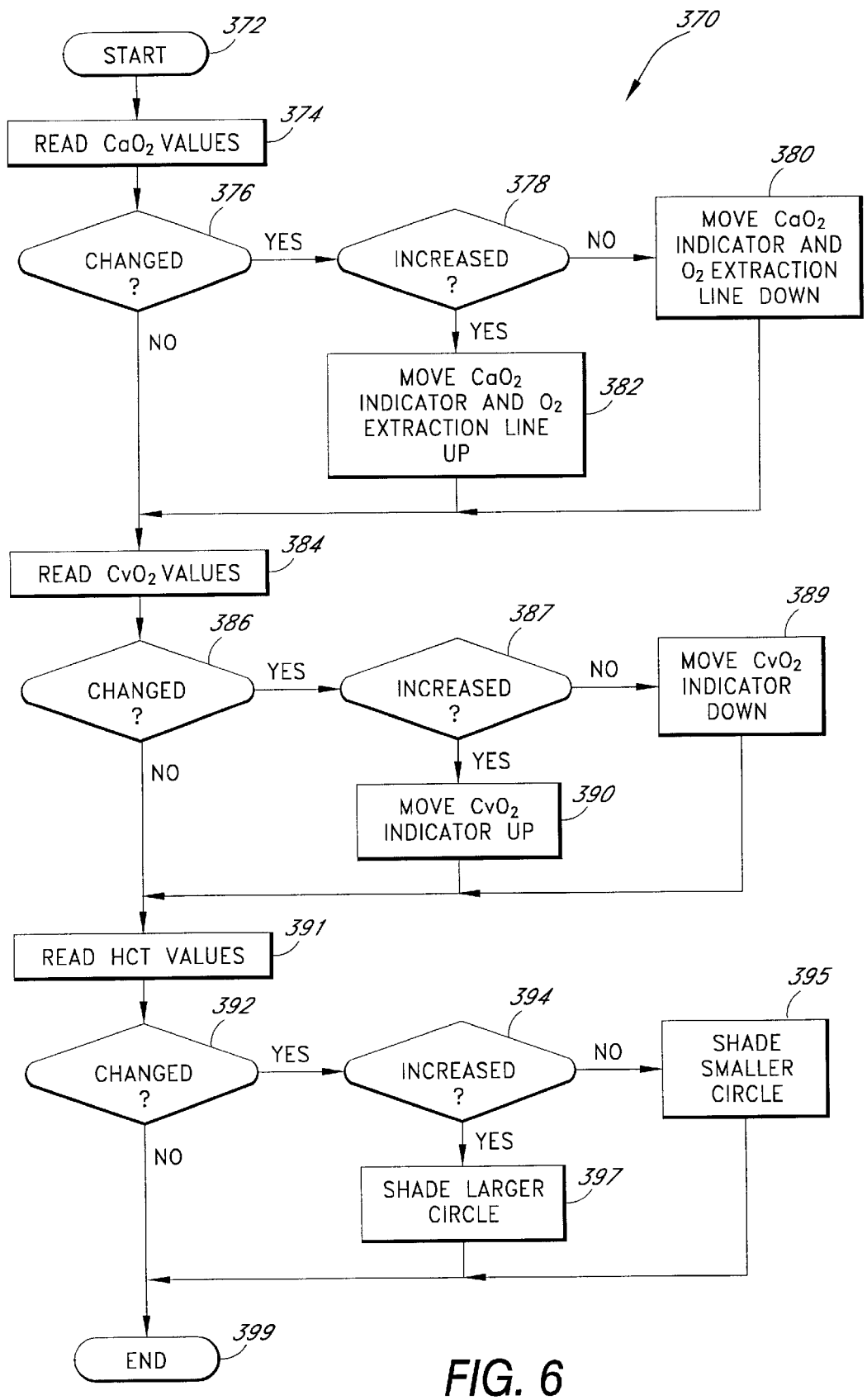
FIG. 6 is a flowchart illustrating one method for updating a display of the red blood cell object from FIG. 5.

Referring now to FIG. 6, a process 370 of updating the red cell object 300 begins at a start state 372. The process 370 then moves to a state 374 wherein the $CaO_2$ value for the patient is read. As discussed above, this value can be read from a data table or from any type of memory storage in the computer system. Once the $CaO_2$ level is read at the state 374, the process 370 moves to a decision state 376 to determine if the $CaO_2$ value has changed from the last sampling. If the $CaO_2$ value has changed, the process 370 moves to a decision state 378 to determine whether the $CaO_2$ value has increased or decreased. If the $CaO_2$ value has increased, the $CaO_2$ indicator 320 and oxygen extraction line 350 are moved up vertically along the Y-axis at a state 382. However, if the $CaO_2$ has decreased, the process 370 moves to a state 380 wherein the $CaO_2$ indicator 320 and oxygen extraction line 350 moved downward along the Y-axis. The process 370 then moves to a state 384 wherein the $CvO_2$ value is read.

A determination is then made at a decision state 386 whether the $CvO_2$ value has changed since the last data sampling. If the value has changed, the process 370 moves to a decision state 387 to determine whether the $CvO_2$ value has increased or decreased. If a determination is made that the $CvO_2$ value has increased, the process 370 moves to a state 390 wherein the $CvO_2$ indicator 330 is moved upwards along its Y-axis. Similarly, if a determination is made at the decision state 387 that the $CvO_2$ value has decreased, the process 370 moves to a state 389 wherein the $CvO_2$ indicator 330 is moved downward along its Y-axis. The process 370 then moves to a state 391 wherein the hemoglobin value of the patient is read.

The process 370 then moves to a decision state 392 to determine whether the hemoglobin value has changed since the last sampling. If a determination is made that the hemoglobin level has changed, the process 370 moves to a decision state 394 wherein a determination is made whether the hemoglobin value has increased or decreased. If the hemoglobin level has increased, the process 370 moves to a state 397 wherein the shaded area 360 is increased in size to indicate a larger quantity of red blood cells in the patient's blood. However, if a determination is made at the decision state 394 the hemoglobin level has decreased, the process 370 moves to a state 395 wherein the shaded areas, 360–362 reduced in circumference. The process 370 then terminates at an end state 399.

B. The Heart Pump Object

Figure 7:
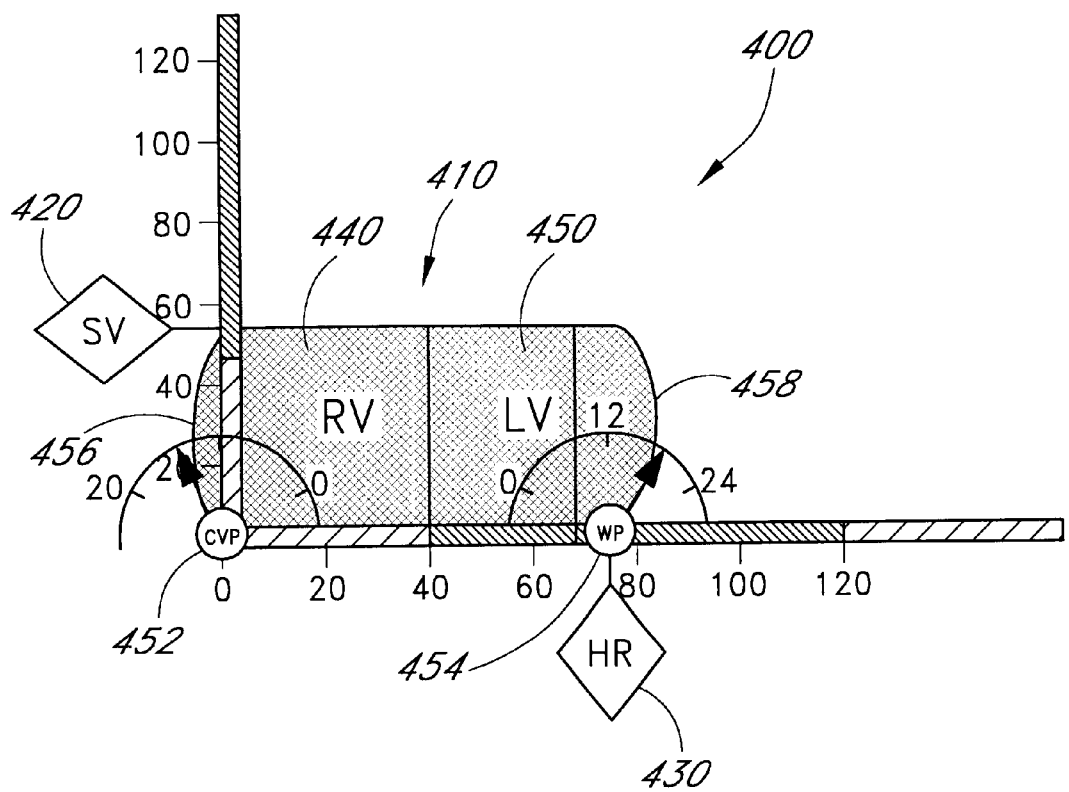
FIG. 7 illustrates one embodiment of a heart pump object.

Referring to FIG. 7, a heart pump object 400 displays the following relationship: Cardiac Output=(Stroke Volume)×(Heart Rate). In one aspect, the heart pump object 400 is displayed as a rectangle 410 wherein the area of the rectangle 410 represents the cardiac output of the patient. The amount of blood pumped with each stroke, the stroke volume (SV) of the heart, is thus represented by a diamond 420 on the Y-axis. The heart rate (HR) is represented as a diamond 430 along the X-axis. With each heart beat, the heart rate and stroke volume are calculated and plotted to this diagram. The rectangle 410 divided into a right ventricular (RV) metaphor 440 and left ventricular (LV) metaphor 450 by dividing the size of the rectangle 410 in half along the X-axis. The shape of a low Stroke Volume ventricle would be reflected by a rectangle 410 is short and wide, while the shape of a bradycardiac ventricle with a normal SV would be indicated by a rectangle 410 is tall and thin.

The filling pressure or volume information, or contractility of the heart chambers (right and left), is presented in the form of a central venous pressure (CVP) analog gauge 452 and Pulmonary Artery Capillary Wedge Pressure (WP) analog gauge 454 located on the X-axis. For both analog meters 452, 454, the 12 o'clock position is defined as normal. Thus, when the CVP and WP are read as normal, the rectangle 410 has squared sides.

However, because the CVP analog meter 452 scribes an arc along the X-axis, if a CVP reading is not normal, the left side 456 of the rectangle 410 will bow in or out. When the left side 456 bows outward due to a high CVP, it represents a distended overfilled right ventricle. Similarly, when the left side 456 bows inward due to a low CVP, it indicates an empty, under-filled right ventricle. As can be imagined, the bulging shape of the left side 456 of the rectangle 410 readily conjures up images of the in vivo heart being overfilled with blood.

When the WP is not normal, the WP analog meter 454 scribes an arc along a right side 458 of the rectangle 410. As the WP increases, the right side 458 bulges outward indicating a swollen, overfilled left ventricle in the patient. In addition, as the WP decreases, the WP analog meter 454 scribes a scalloped arc along the right side 458 so that the left ventricle is illustrated as an empty, unfilled ventricle. The right side 458 and the left side 456 correspond with the image of the heart seen with a long-axis four chamber view using transesophageal echo-cardiography. Thus, it is readily apparent to an anesthesiologist when the right or left side ventricles are either under-filled or overfilled during surgery by noting not only the relative dimensions of the rectangle 410, but also the shapes of its sides.

Figure 8A:
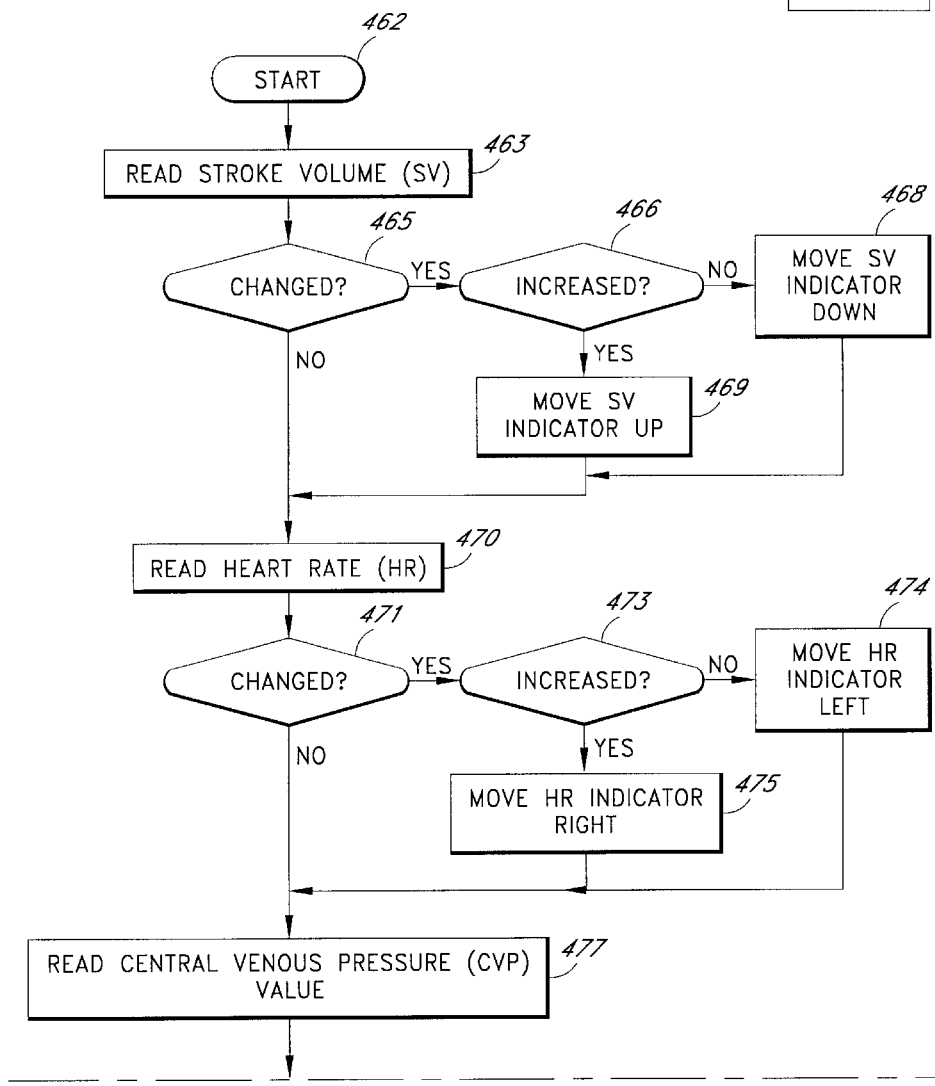
FIG. 8 is a flowchart illustrating one method for updating a display of the heart pump object from FIG. 7.
Figure 8B:
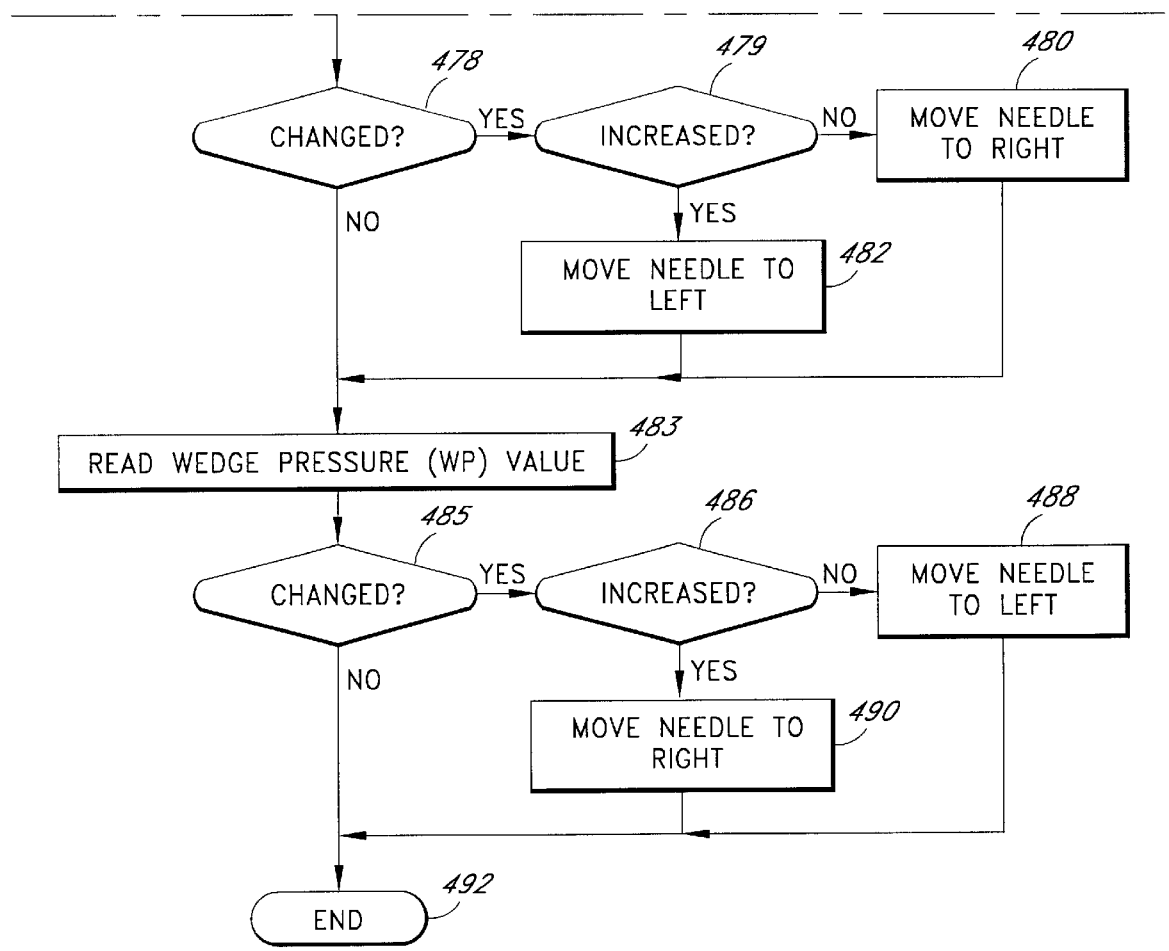

Referring now to FIG. 8, the process 460 modulating the heart pump object 400 described. The process 460 begins at a start state 462, and then moves to a state 463 where the stroke volume (SV) is read. As can be imagined, stroke volume can be read from a table or buffer in the computer system. The process 460 then moves to a decision state 465 to determine whether the stroke volume has changed since the last reading. If the stroke volume has changed, the process 460 moves to a decision state 466 to determine whether the stroke volume has increased or decreased.

If the stroke volume has decreased, the process 460 moves to a state 468 wherein the stroke volume indicator 420 moved downward along the Y-axis. As illustrated in FIG. 7, as the stroke volume indicator 420 moved downward along the Y-axis, the shaded rectangle 410 reduced in height. If a determination is made at the decision state 466 the stroke volume has increased, the process 460 moves to a state 469 wherein the stroke volume indicator 420 moved upward along the Y-axis This, in turn, increases the height of the shaded rectangle 410. The process 460 then moves to a state 470 wherein the patient's heart rate is read. A determination is then made at a decision state 471 whether the heart rate has changed from the last reading.

If the heart rate has changed since the last reading, a determination is made at a decision state 473 whether the heart rate has increased or decreased. If the heart rate has decreased, the process 460 moves to a state 474 wherein the heart rate indicator is moved to the left along the X-axis of the heart pump object 400. However, if a determination is made at the decision state 473 the heart rate has increased, the process 460 moves to a state 475 wherein the heart rate indicator 430 moved to the right along the X-axis of the heart pump object 400. As can be imagined upon review of FIG. 7, as the heart rate indicator 430 moved horizontally along the X-axis, the width of the shaded rectangle 410 increased and decreased accordingly.

The process 460 then moves to a state 477 wherein the central venous pressure (CVP) value is read. A determination is then made at a decision state 478 whether the CVP has changed since the last reading. If the CVP has changed, a determination is made at a decision state 479 whether the CVP has increased or decreased. If the CVP has decreased, the process 460 moves to a state 480 wherein the analog CVP gauge 452 moved to the right along its predetermined arc. As discussed above, as the CVP analog gauge 452 moved to the right along its arc, the shape of the right ventricular metaphor 440 altered to indicate a less filled heart chamber.

If a determination was made at the decision state 479 the CVP has increased, the process 460 moves to a state 482 wherein the CVP analog gauge 452 moved to the left along its arc, the left side 456 the right ventricular metaphor 440 begins bulging outward to indicate a swollen heart chamber. The process 460 then moves to a state 483 wherein the wedge pressure (WP) value is read.

The process 460 then moves to a decision state 485 to determine whether the wedge pressure has changed since the last reading. If the wedge pressure has changed, a determination is made at a decision state 486 whether the value of the wedge pressure has increased or decreased. If the value of the wedge pressure has decreased, the process 460 moves to a state 488 wherein the wedge pressure analog gauge 454 moved to the left along its predetermined arc. As the analog gauge 454 moved left, the side 458 the left ventricular metaphor 450 becomes more concave indicating a less-filled heart chamber. In addition, as the value of the patient's heart rate (HR) changes, the WP analog gauge is slid left to right along the X-axis. As the heart rate increases, the WP analog gauge slides right, while as the HR decreases, the WP analog gauge slides left.

However, if a determination is made at the decision state 486 the wedge pressure has increased, the process 460 moves to a state 490 wherein the wedge pressure gauge 454 moved to the right along its predetermined arc. As can be envisioned upon review of the heart pump object 400, as the wedge pressure analog gauge 454 moved to the right, the edge 458 the left ventricular metaphor 450 curved outward indicating a bulging or swollen heart chamber. The process 460 then ends at an end state 492.

C. The Vascular Resistor Object

Figure 9:
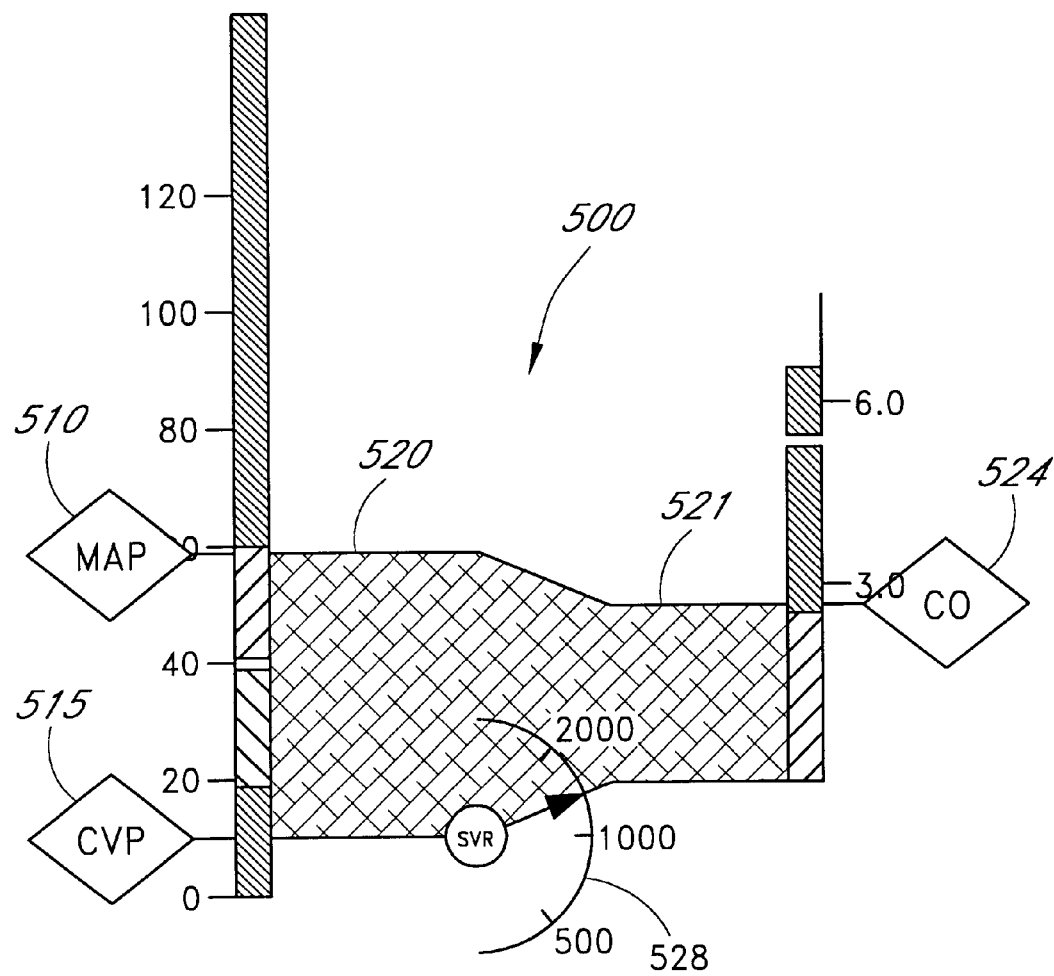
FIG. 9 illustrates one embodiment of a vascular resistor object.

Referring to FIG. 9, a vascular resistor object 500 used to display the blood flow equivalent of Ohm's Law. This display is used by medical personnel to optimize the hemodynamic physiology of patients during surgery. The vascular resistor object 500 represents the following equation: (Mean Arterial Pressure)−(Central Venous Pressure)=(Cardiac Output)×(Systemic Vascular Resistance). The data is displayed in the object 500 such that the shape of a "pipe" emerges with flow from left to right. Two lineal scales relating to the pressure gradient for blood flow and the actual cardiac output in liters per minute are shown as a function of the systemic vascular resistance (SVR) such that a "pipe" metaphor emerges.

A set of two Y-axes are used to produce the vascular resistor object 500. A left Y-axis includes a mean arterial pressure (MAP) indicator 510 and a central venous pressure (CVP) indicator 515. A blood input area 520 between the MAP indicator 510 and CVP indicator 515 indicates "inflow" of blood into the pipe. In contrast, a blood output area 521 indicates the "outflow" of blood from the pipe. A right Y-axis includes a cardiac output (CO) indicator 524 reflects the calculated cardiac output of the patient. This is the outflow portion of the pipe. An SVR analog gauge 528 disposed on the X-axis linking the right and left axes. If the SVR is normal, the SVR gauge is set at the 3 o'clock position. If the SVR is low, the SVR meter points downward reflecting the fact that the pipe is open. In contrast, a high SVR reading causes the gauge to move upward indicating a more closed pipe as shown in FIG. 9.

To translate into physiological terms, as the SVR increases, the flow of blood is reduced, as indicated by the constricted pipe. As the SVR decreases, the flow of blood is increased, as indicated by a more open pipe. The MAP indicator 510 can also affect the model, since an increasing MAP widens the inflow so more overall blood flow is found. As can be imagined, the vascular resistor object 500 closely reflects the actual physiology of the patient. It is thus an intuitive object for deciphering complex situations in a patient.

Figure 10A:
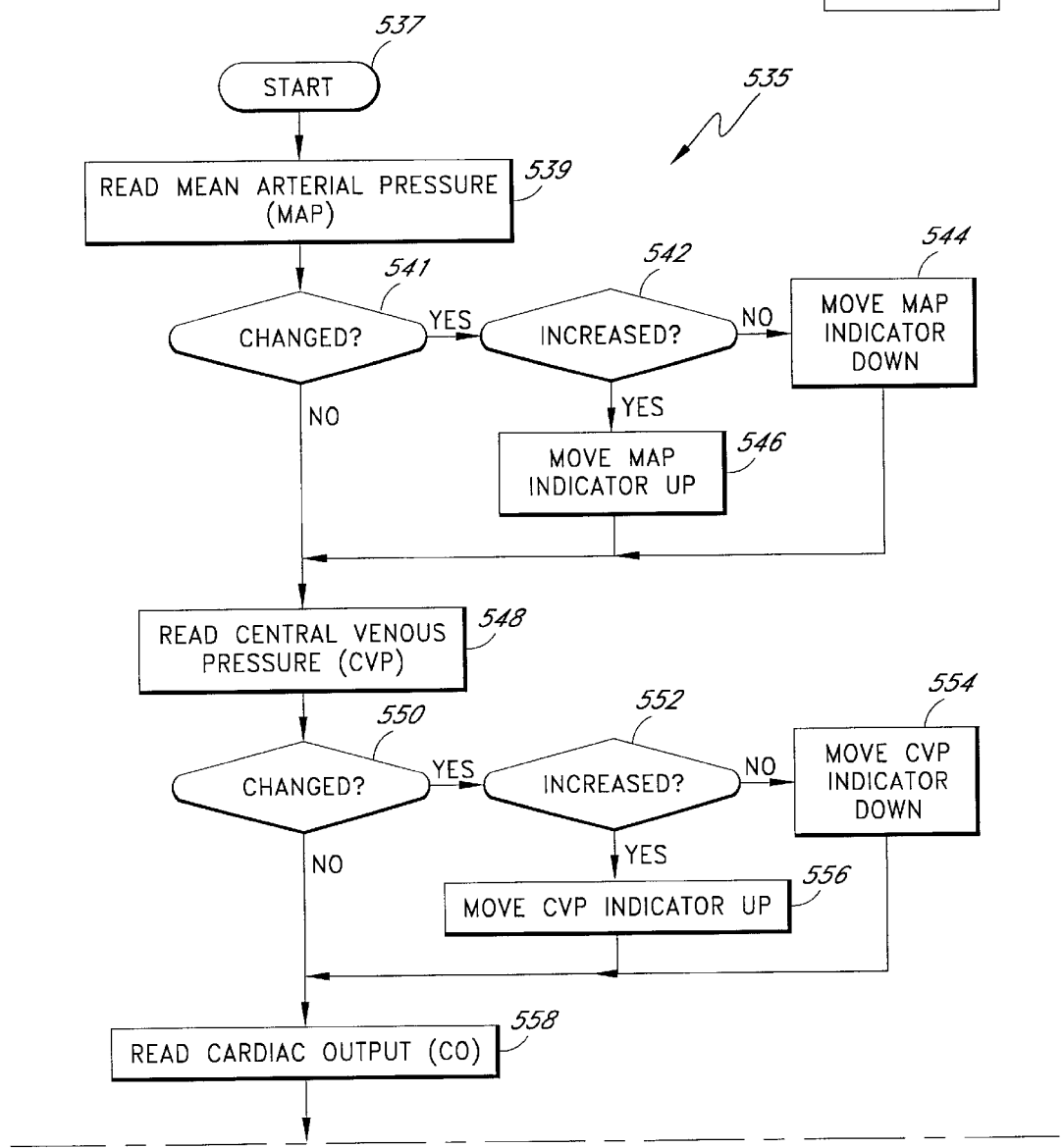
FIG. 10 is a flowchart illustrating one method for updating a display of the vascular resistor object from FIG. 9.
Figure 10B:
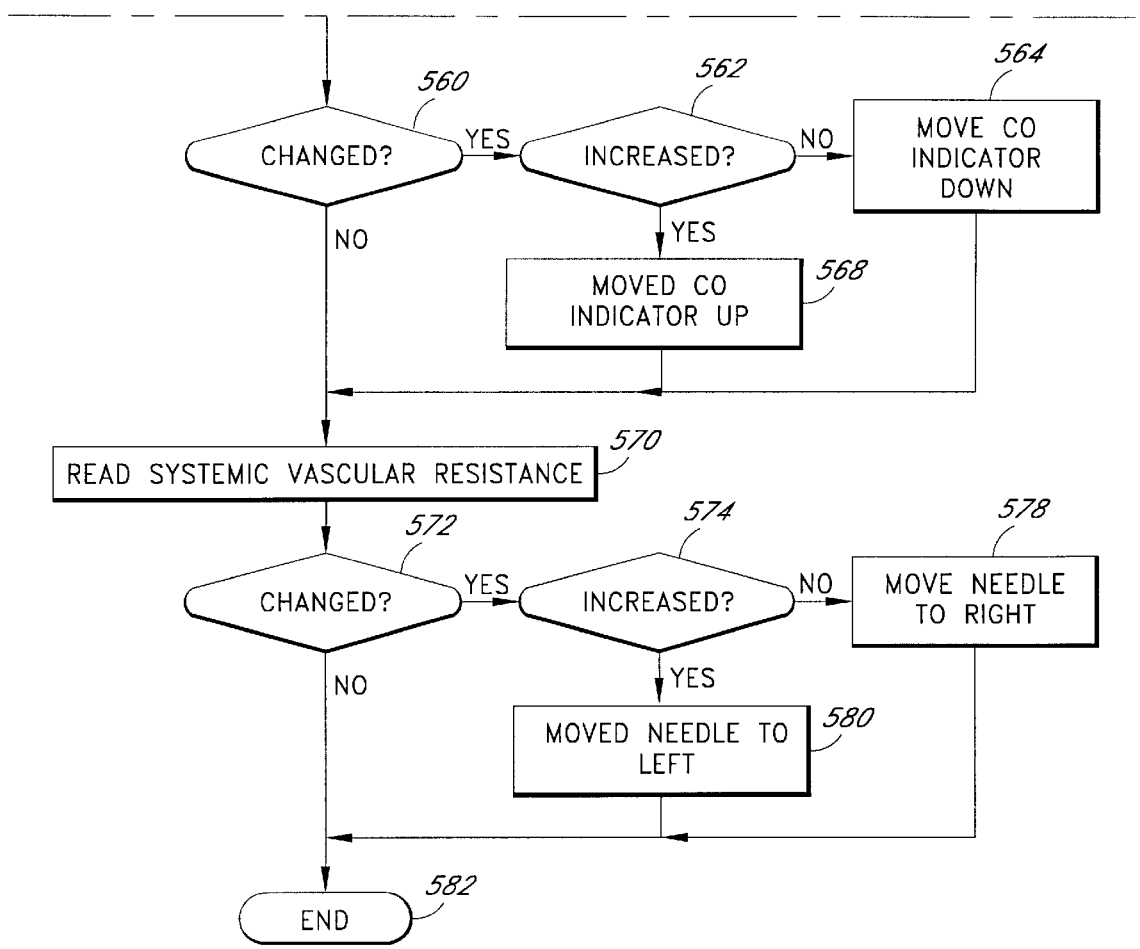

Referring to FIG. 10, a process 535 updating the vascular resistor object 500 described. The process 535 begins at a start state 537 and then moves to a state 539 wherein the mean arterial pressure (MAP) is read. A determination is then made at a decision state 541 whether the MAP has changed since the last reading. If the MAP has changed, the process 535 moves to a decision state 542 to determine whether the MAP has increased or decreased. If the MAP has decreased, the process 535 moves to a state 544 wherein the MAP indicator 510 moved downward along the Y-axis of the vascular resistor object 500. However, if a determination is made at the decision state 542 the MAP has increased, the process 535 moves to a state 546 wherein the MAP indicator 510 moved upwards along the X-axis. As can be seen upon review of FIG. 9, as the MAP indicator 510 moves up and down along the X-axis the area 520 becomes larger or smaller, respectively.

The process 535 then moves to a state 548 wherein the central venous pressure of the patient is read. A determination is then made at a decision state 550 whether the CVP has changed since the last reading. If the CVP has changed, the process 535 moves to a state 552 to determine whether the CVP has increased or decreased. If the CVP has decreased, the process 535 moves to a state 554 wherein the CVP indicator 515 moved down. If a determination is made at the decision state 552 the CVP has increased, then the process 535 moves to a state 556 wherein the CVP indicator 515 moved up. The process 535 then moves to a state 558 wherein the cardiac output (CO) is read.

A determination is then made at a decision state 560 whether the cardiac output has changed since the last reading. If the cardiac output has changed, the process 535 moves to a decision state 562 to determine whether the cardiac output has increased or decreased. If the cardiac output has decreased, the process 535 moves to a state 564 wherein the cardiac output indicator 524 moved down along its Y-axis. However, if a determination was made at the decision state 562 the cardiac output had increased, the process 535 moves to a state 568 wherein the cardiac output indicator 524 moved up along its Y-axis. The process 535 then moves to a state 570 wherein the systemic vascular resistance is measured.

A determination is then made at a decision state 572 whether the systemic vascular resistance (SVR) has changed since the last reading. If the SVR has changed, a determination is then made at a decision state 574 whether the SVR has increased or decreased since the last reading. If the SVR has decreased, the process 535 moves to a state 578 wherein the SVR analog gauge 528 moved to the right along its predetermined arc. Thus, as the patient's vascular resistance is decreased, the vascular resistor object 500 indicates a greater area of outward flow. If a determination is made at the decision state 574 the SVR has increased, the process 535 moves to a state 580 wherein the SVR analog gauge 528 moved to the left along its predetermined arc. As indicated in FIG. 9, as the SVR analog gauge 528 moves to the left, the output area 521 the vascular resistor object 500 reduced. The process 535 then terminates at an end state 582.

D. The Metabolism Object

Figure 11:
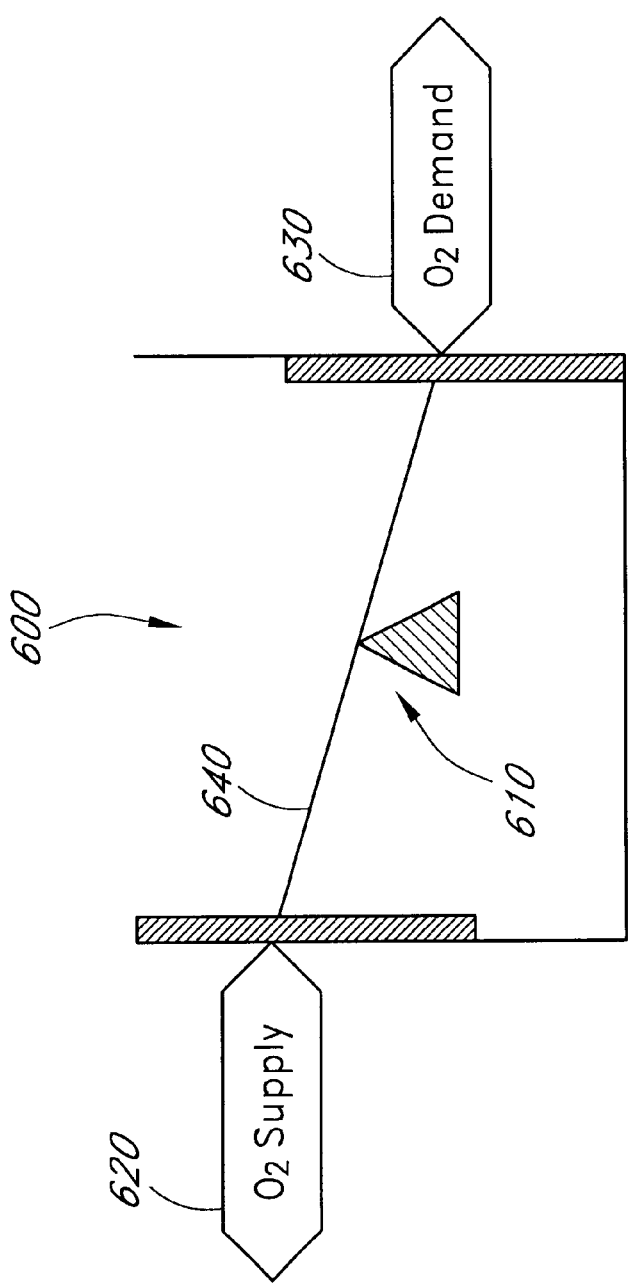
FIG. 11 illustrates one embodiment of a metabolism object.

Referring to FIG. 11, a metabolism object 600 illustrated. The metabolism object 600 displays the relationship of oxygen delivery ($DO_2$) by illustrating the equation: (Oxygen Delivery)=(Cardiac Output)×(Arterial Oxygen Content).

In addition, the metabolism object 600 also illustrates Oxygen Utilization ($VO_2$) by the equation: (Oxygen Utilization)=(Arterial Oxygen Content)−(Venous Oxygen content).

In a normal patient, the oxygen supply greatly exceeds the oxygen utilization. Thus, a fulcrum or pivot 610 used to illustrate the balance between an oxygen supply ($DO_2$) indicator 620 and oxygen demand ($VO_2$) indicator 630. A lever or balance line 640 runs between the $DO_2$ indicator 620 and $VO_2$ indicator 630 and balanced on the pivot 640. The slope of the $DO_2$ to $VO_2$ used to indicate the "balance" or relationship between $DO_2$ and $VO_2$ more readily apparent to the physician. In addition, anaerobic metabolism and its associated acidosis cause the scale to tip in the wrong direction to indicate that although oxygen is being supplied, the cells are not using it.

Figure 12:
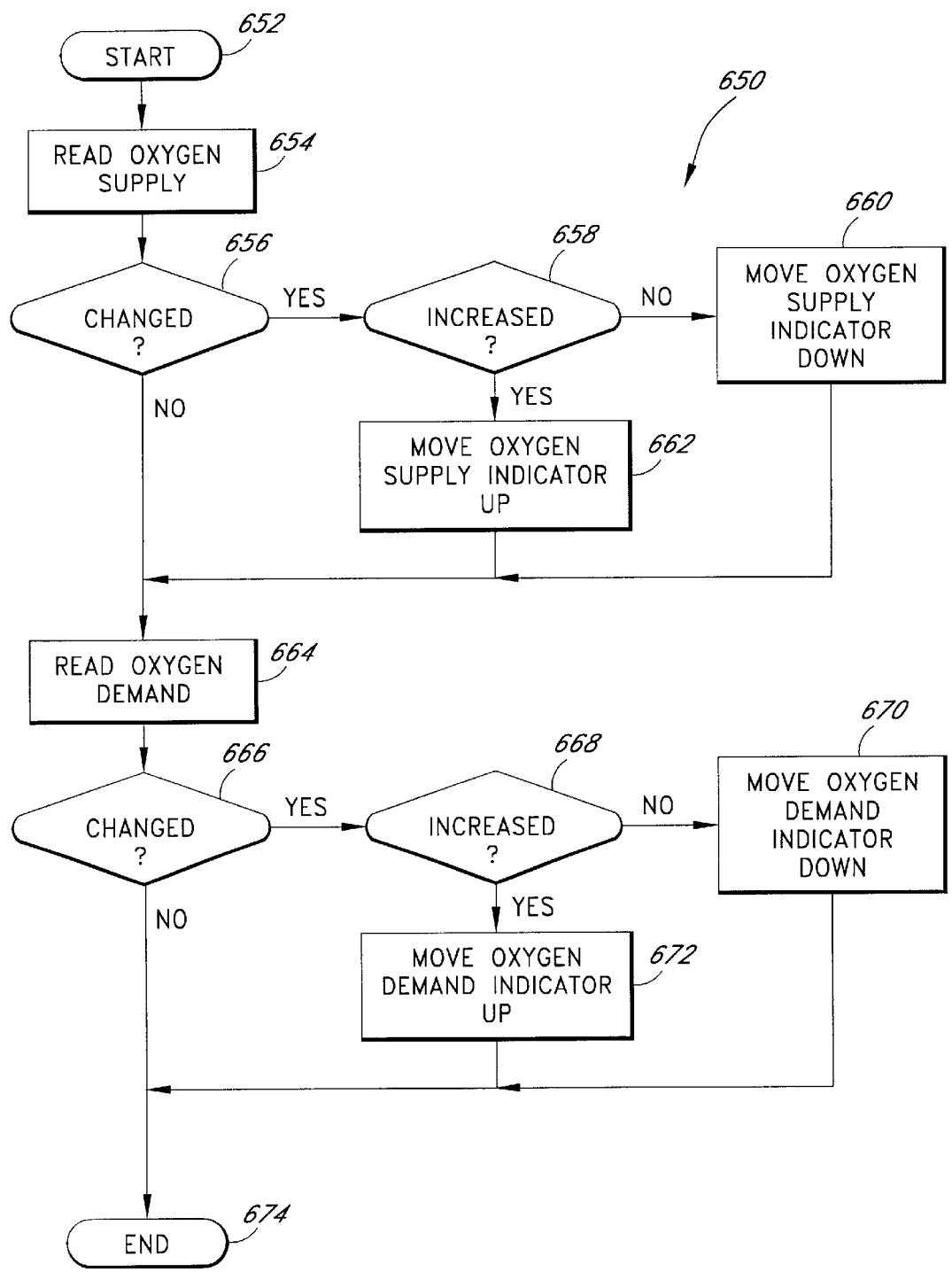
FIG. 12 is a flowchart illustrating one method for updating a display of the metabolism object from FIG. 11.

Referring to FIG. 12, a process 650 updating the metabolism object 600 described. The process 650 begins at a start state 652 and then moves to a state 654 where the oxygen supply of the patient's blood is read. The process 650 then moves to a decision state 656 to determine whether the oxygen supply value ($DO_2$) has changed since the last reading. If the oxygen supply value has changed, the process 650 moves to a decision state 658 to determine whether the oxygen supply has increased or decreased in the patient's blood. If the value of the oxygen supply has decreased, the process 650 moves to a state 660 wherein the oxygen supply indicator 620 (FIG. 11) is moved downward along its Y-axis. However, if the oxygen supply value has increased, the process 650 moves to a state 662 wherein the oxygen supply indicator 620 moved upward along its Y-axis. The process 650 then moves to a state 664 to read the oxygen demand value ($VO_2$) in the patient.

Once the oxygen demand value has been read at the state 664, the process 650 moves to a state 666 to determine whether the oxygen demand value has changed since the last reading. If the oxygen demand value has changed, the process 650 moves to a decision state 668 to determine whether the oxygen demand value has increased or decreased. If the oxygen demand value has decreased, the process 650 moves to state 670 wherein the oxygen demand indicator 630 (FIG. 11) is moved downward along its Y-axis. However, if a determination is made at the decision state 668 the oxygen demand has increased, the process 650 moves to a state 672 wherein the oxygen demand indicator 630 moved upwards. The process 650 then terminates at an end state 674.

E. Grouping the Data Objects into a Unified Display

Figure 13:
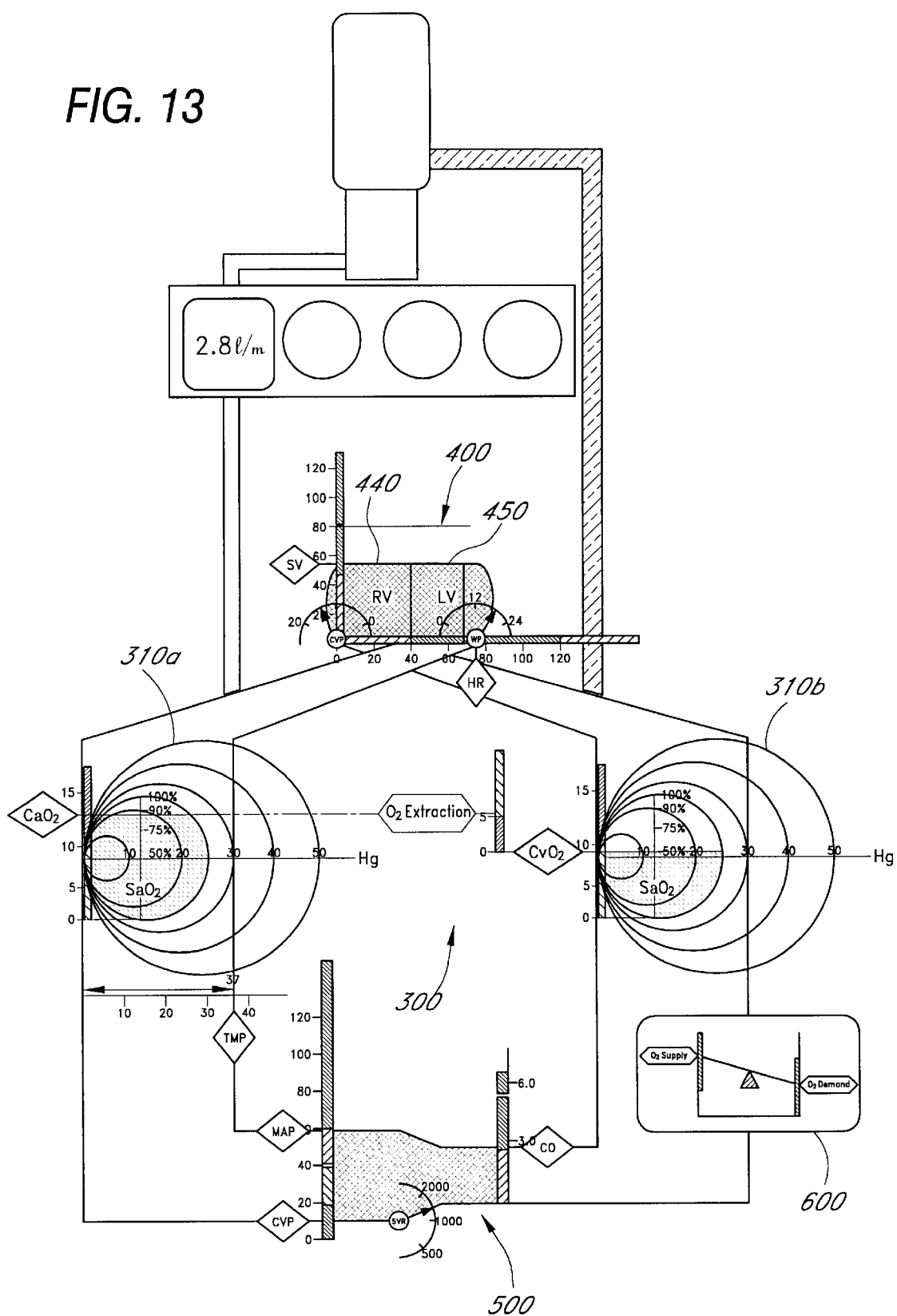
FIG. 13 illustrates a display representing a circuit for displaying physiological data. In one embodiment, the display includes a heart pump object, vascular resistor object, red blood cell object and metabolism object.

FIG. 13 illustrates one embodiment of a display having each of the data objects 300, 400, 500 and 600. The data objects are arranged in the pattern shown to create a circuit illustrating that oxygen is carried from the left ventricle of the heart pump object 400, into an arterial blood cell 310*a*, through the vascular resistor 500 (e.g. capillary cells) where oxygen is unloaded at the tissue cells (object 600) and returns to through a venous blood cell 310*b* to the right ventricle 440. Thus, a complete illustration of the oxygenation cycle is provided in a very intuitive manner by the relationship of objects in FIG. 13.

F. Boundary information

All of the scales used to map values to indicators and gauges preferably have normal and abnormal zones (which can be and preferably are colored). Thus, the indicators can change colors when a patient is entering an abnormal zone. The alert zones are selectable so that the physician can make the warnings more or less stringent based on the physiology of the particular patient. In this manner, the user sets the value above or below the critical thresholds at the point she wishes to be alerted. When the alert zone is entered, an indicator begins to change color, or start flashing in a graded manner such that the brighter the red color of the indicator, the closer the value is to the threshold. Of course, the indicators could change in many different ways to alert the physician that an abnormal zone has been entered. This invention should not be construed to be limited by any particular notification method.

G. Confidence Interval Information

When the precision and bias of a measured data channel are known, the pointer tip is preferably centered on the appropriate value but will have a thickness which touches the scale and which covers the know error associated with that datum. This creates a pointer which changes color and which enters danger zones based on worst case scenarios.

H. Trend Information

The trend information, for example, includes a set of "cards" on a z-axis or on a time scale on the X-axis. The values over a time interval selected by the user are displayed and the resolution of the data (sampling rate) is made visible.

L Normalization of Information.

Due to tremendous inter-patient variability and the changing patient physiologic state in settings like surgery (i.e., the definition of what is normal changes) the values which represent frames of reference can be re-sized and re-scaled on command. For example a "normal" SVR setting for the SVR object 550 FIG. 9 can default to 1000 at the 3 o'clock position. However if a patient normally has a SVR of 2000, this function can reset the normal 3 o'clock position of the SVR analog gauge to 2000.

J. Artifact Detection and Signal Quality Information.

Viewing the analog signal of a given data channel provides a great deal of information about signal quality. Pop-up windows next to the data pointers are thus available, similar to the trend windows, to detect noise or artifact information. The pop-up windows are activated by, for example, clicking on a data pointer.

K. Patient Disease Information

The data regarding disease states can be saved, if desired, to reset boundary defaults. For example, hypertension shifts the autoregulatory curve to the right such that most doctors keep the blood pressure in a higher range than usual.

L. Examples of Disease States

Figure 14:
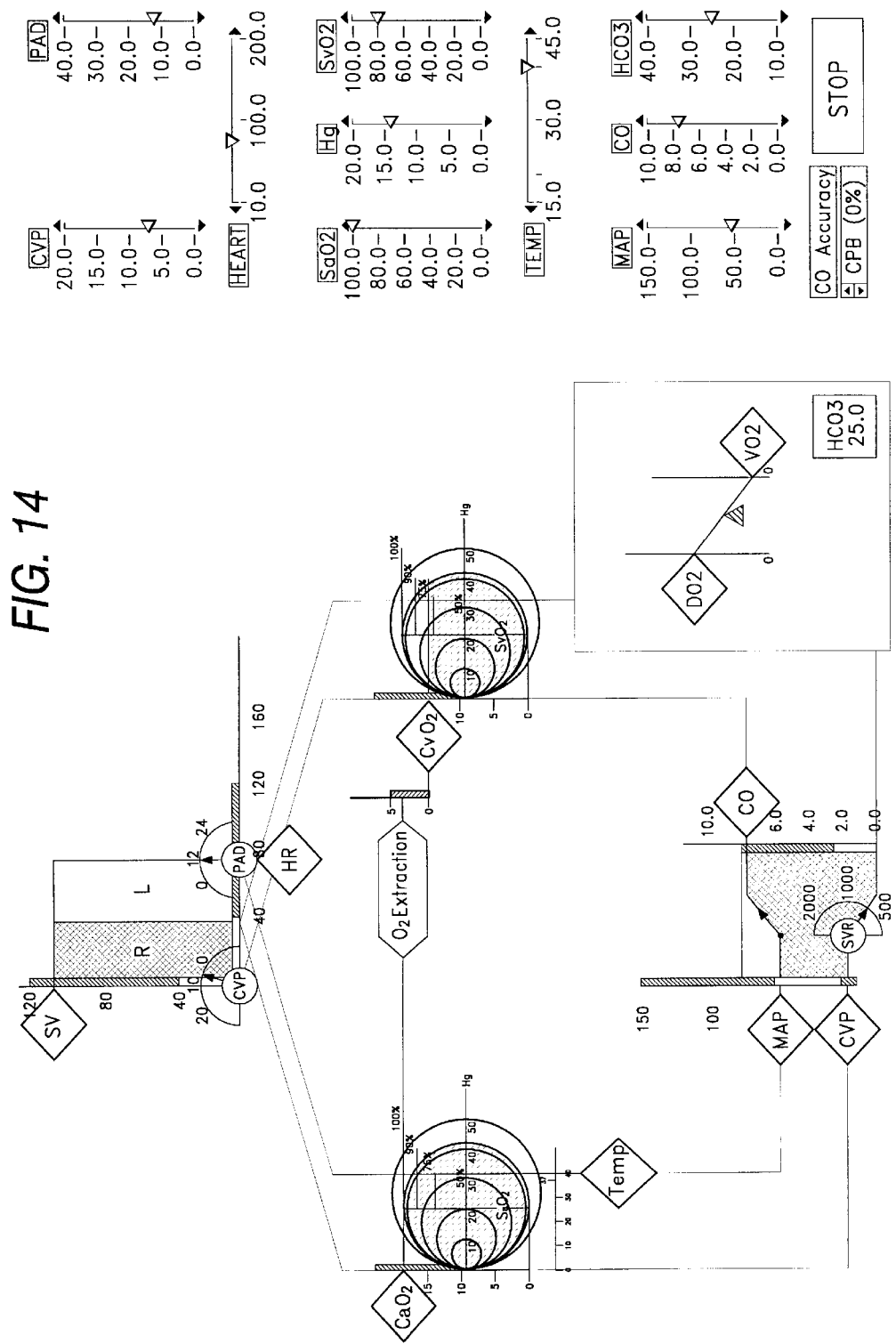
FIG. 14 illustrates one embodiment of the circuit during anaphylaxis or sepsis.
Figure 15:
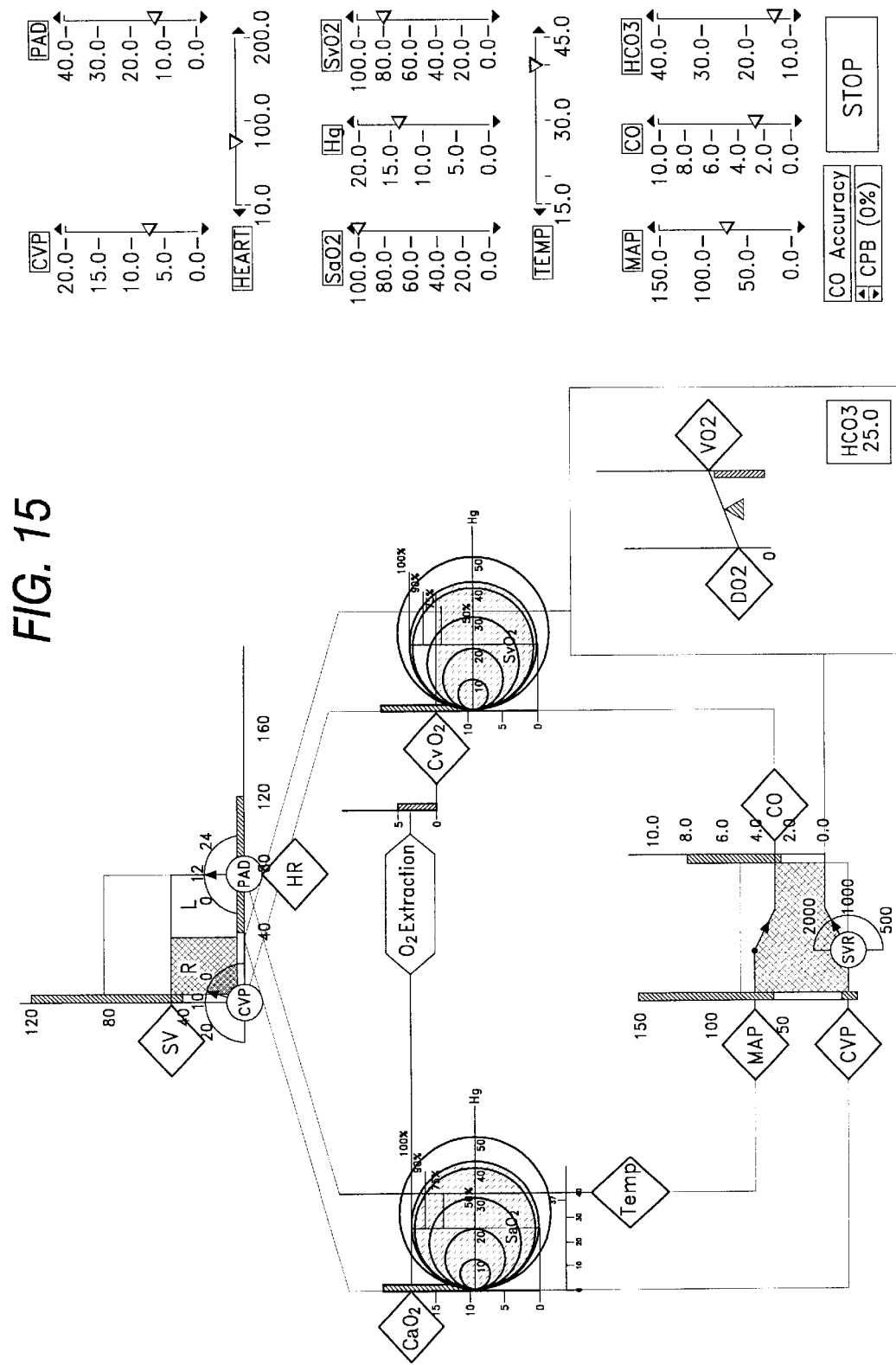
FIG. 15 illustrates one embodiment of the circuit during cellular acidosis.
Figure 16:
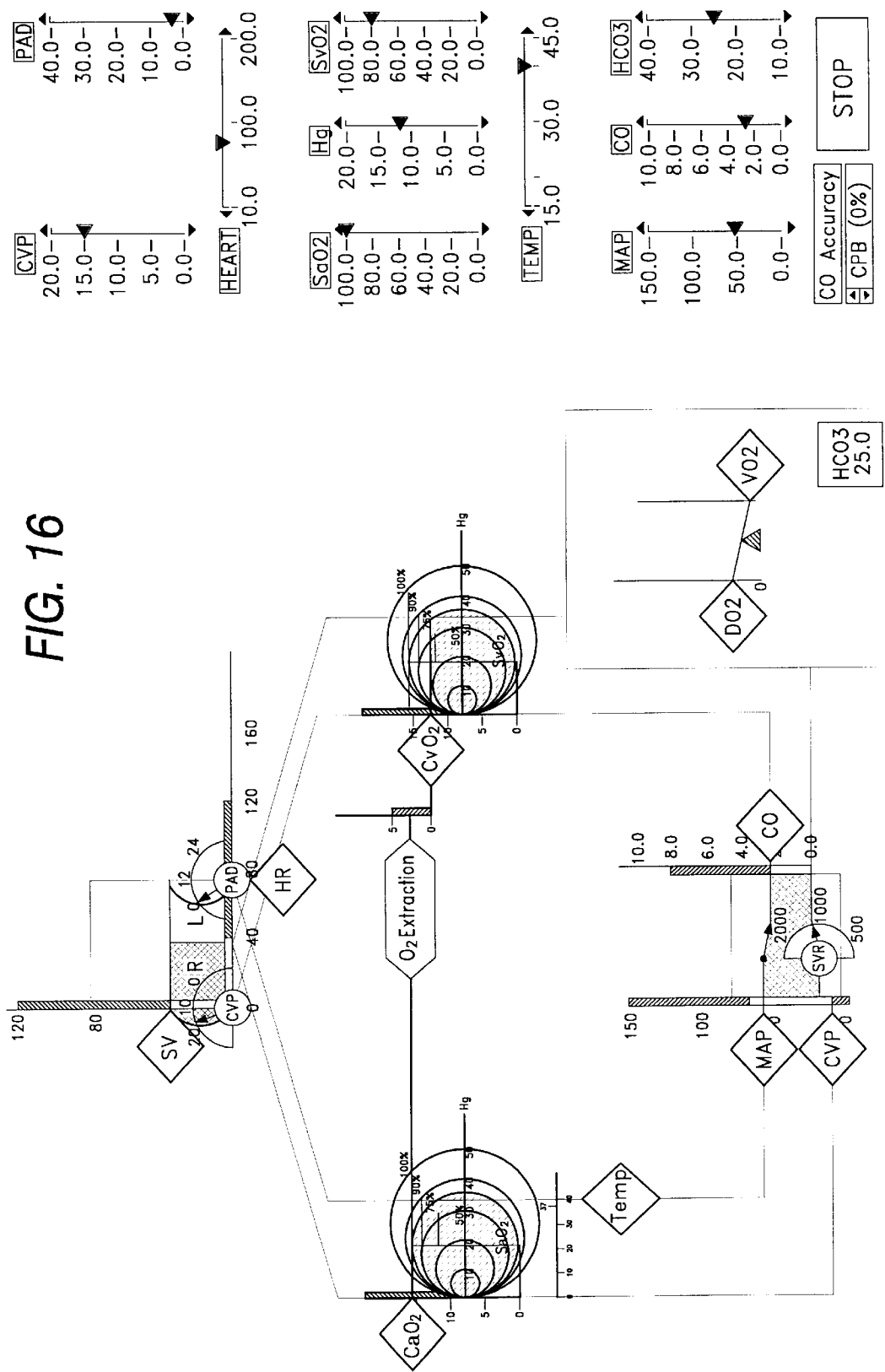
FIG. 16 illustrates one embodiment of the circuit during a pulmonary embolism.

FIG. 14 illustrates one embodiment of the circuit display during anaphylaxis or sepsis. FIG. 15 illustrates one embodiment of the circuit display during cellular acidosis. FIG. 16 illustrates one embodiment of the circuit display during a pulmonary embolism.

Pilot Study

A pilot study was performed which attempted to test the hypothesis that the set of object displays developed will improve the ability of anesthesiologists to solve problems such as acute hypotension.

Study subjects: study subjects were all in their final year of training or attending level anesthesiologists (N=10). Each physician had over three months experience providing cardiac anesthesia.

Test Parameters:

Data sets were generated for five patterns of shock (anaphylactic, bradycardic, hypovolemic, cardiogenic, and secondary to pulmonary embolus) and five patterns of near shock (MAP-CVP was 60–70 mm Hg but otherwise were represented the five shock states). The data sets were used to generate twenty "flash cards" (one set standard display cards and one set of graphical display cards). FIG. 14 is an example of one flash card from the study indicating anaphylaxis.

Hardware consisted of a computer workstation with a 21 inch touch-screen monitor. The study test was a software application written in LabView. The application "shuffles" the cards to randomize the order in which they are presented to the study subject. When the application is started (constituting a trial), a screen with a "next" button hides the upcoming display. When the study subject touches this button, the first display picture appears and the subject must choose from five buttons (No Problem, Anaphylaxis, Bradycardia, Hypovolemia, Ischemia, and Pulmonary Embolus). The "next" button screen then appears and touching the button advances the next card. This is done for all twenty cards. The internal clock in the computer is used to measure problem (shock) recognition speed, accuracy and pattern recognition (etiology) speed and accuracy. Study subjects completed surveys pre- and post-testing.

We discovered that the residents were able to recognize problems 30 percent faster in comparison to previous displays. In addition, the residents were able to identify patient patterns 25% faster than with previous displays. We found that there was no difference in accuracy. The total training time was approximately 30 minutes.

Conclusion

Current displays for presenting physiologic data to physicians working in critical care medicine force the physicians to perform a great deal of cognitive work to interpret that data. The display system disclosed herein provides visual memory cues and maps complex data graphically to displays which match the mental model physicians used to interpret oxygen-transport physiology.

The system receives analog signals which drives the display real-time. Alarm conditions can be set by the physician and are visible at all times. The danger zones which create shades of red in the data pointer are easy for physicians to understand (physicians are accustomed to using fuzzy logic for interpreting data). In addition, the way that data elements have been constructed and displayed produces perceptual diagrams. The shapes themselves convey very high-level information regarding oxygen-transport physiology to physicians.

I claim:

1. A data object visually representing the vascular resistance to blood flow in a patient wherein the object is visually representative of the mean arterial pressure (MAP) of the patient's blood and the cardiac output (CO) of a patient's heart; wherein the data object is further representative of the central venous pressure (CVP) of a patient's blood and the systemic vascular resistance (SVR) of the patient's blood.

2. The data object of claim 1, wherein the data object is in the shape of a pipe.

3. The data object of claim 2, wherein one end of the of the pipe dilates or constricts relative to the other end of the pipe as the mean arterial pressure or cardiac output of the patient fluctuates.

4. A data object visually representing the vascular resistance to blood flow in a patient wherein:

the data object is visually representative of the mean arterial pressure (MAP) of the patient's blood, the cardiac output (CO) of a patient's heart; and the data object is located between two parallel Y-axes and the first and left Y-axis includes a mean arterial pressure (MAP) indicator and a central venous pressure (CVP) indicator.

5. The data object of claim 4, wherein the second and right Y-axis includes a cardiac output (CO) indicator which reflects the cardiac output (CO) of the patient.

6. The data object of claim 4, wherein a systemic vascular resistance (SVR) meter is disposed along an X-axis in-between and linking the Y-axes wherein with a normal SVR reading the SVR meter reads at the 3 o'clock position and wherein with a low SVR reading the SVR meter points downward from the 3 o'clock position causing the object to expand on its right side and with a high SVR reading the SVR meter points upward from the 3 o'clock position causing the object to contract on its right side.

7. An object display comprised of a plurality of objects for visually displaying the physiological status of a patient comprising:

an object for displaying the level of oxygenation of a patient's blood:

an object for representing the cardiac output of a patient's heart;

an object for representing the vascular resistance of blood flow in a patient in the shape of a pipe, and an object for displaying the amount of oxygen delivery to a patient.

8. The object display of claim 7, wherein the object for representing the vascular resistance of blood flow is further representative of the central venous pressure (CVP) of a patient's blood and the systemic vascular resistance (SVR) of the patient's blood.

9. The object display of claim 8, wherein one end of the of the pipe dilates or constricts relative to the other end of the pipe as the mean arterial pressure or cardiac output of the patient fluctuates.

10. The object display of claim 7, wherein the object for representing the vascular resistance of blood flow is located between two parallel Y-axes wherein the first and left Y-axis includes a mean arterial pressure (MAP) indicator and a central venous pressure (CVP) indicator.

11. The object display of claim 10, wherein the second and right Y-axis includes a cardiac output (CO) indicator which reflects the cardiac output (CO) of the patient.

12. The object display of claim 10, wherein a systemic vascular resistance (SVR) meter is disposed along an X-axis in-between and linking the Y-axes wherein with a normal SVR reading the SVR meter reads at the 3 o'clock position and wherein with a low SVR reading the SVR meter points downward from the 3 o'clock position causing the object to expand on its right side and with a high SVR reading the SVR meter points upward from the 3 o'clock position causing the object to contract on its right side.

\* \* \* \* \*